United States Patent
Paramasivan et al.

(10) Patent No.: US 11,989,675 B2
(45) Date of Patent: May 21, 2024

(54) EFFICIENT SURGICAL CENTER WORKFLOW PROCEDURES

(71) Applicant: Stryker Corporation, Kalamazoo, MI (US)

(72) Inventors: Ramanan Paramasivan, San Jose, CA (US); Brian Bailey, San Jose, CA (US); Suraj Bhat, Fremont, CA (US); William Huei Liang Chang, Milpitas, CA (US); Benjamin H. Feingold, Tucson, AZ (US); Steve Hanning, Ben Lomond, CA (US); Amit Mahadik, San Jose, CA (US); John T. Shen, San Jose, CA (US); Murthy Vinjamuri, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/062,493

(22) Filed: Oct. 2, 2020

(65) Prior Publication Data
US 2021/0019672 A1 Jan. 21, 2021

Related U.S. Application Data

(62) Division of application No. 15/592,608, filed on May 11, 2017, now abandoned.
(Continued)

(51) Int. Cl.
*G16H 40/20* (2018.01)
*A61B 17/00* (2006.01)
(Continued)

(52) U.S. Cl.
CPC ......... *G06Q 10/0633* (2013.01); *A61B 17/00* (2013.01); *G16H 10/60* (2018.01);
(Continued)

(58) Field of Classification Search
CPC .... G16H 40/20; G16H 10/60; G06Q 10/0633; G06V 30/10; A61B 17/00; A61B 2017/00057
(Continued)

(56) References Cited

U.S. PATENT DOCUMENTS 5,740,801 A 4/1998 Branson
9,258,522 B2 2/2016 Beutter et al.
(Continued)

FOREIGN PATENT DOCUMENTS

JP 2002-119520 A 4/2002

OTHER PUBLICATIONS

Paramasivan et al., U.S. Office Action dated Jun. 2, 2020, directed to U.S. Appl. No. 15/592,608; 21 pages.
(Continued)

*Primary Examiner* — Robert W Morgan
*Assistant Examiner* — Liza Tony Kanaan
(74) *Attorney, Agent, or Firm* — Morrison & Foerster LLP

(57) ABSTRACT

A method of providing a visual indication that information is being saved or broadcast includes providing at least one recording device for obtaining the information, providing a system for saving and/or broadcasting the information obtained from the at least one recording device, providing at least one monitor for viewing the information, providing a plurality of visual indications, and activating the plurality of visual indications when the information is being saved or broadcast.

18 Claims, 17 Drawing Sheets

Related U.S. Application Data

(60) Provisional application No. 62/337,602, filed on May 17, 2016.

(51) Int. Cl.
   *G06Q 10/0633* (2023.01)
   *G16H 10/60* (2018.01)
   *G06V 30/10* (2022.01)

(52) U.S. Cl.
   CPC .... *G16H 40/20* (2018.01); *A61B 2017/00057* (2013.01); *G06V 30/10* (2022.01)

(58) Field of Classification Search
   USPC .......................................................... 705/2–3
   See application file for complete search history.

(56) References Cited

U.S. PATENT DOCUMENTS

| | | | |
|---|---|---|---|
| 2004/0119832 A1* | 6/2004 | Schaffner | H04N 5/222 348/E5.022 |
| 2006/0142739 A1* | 6/2006 | DiSilestro | A61B 90/90 606/1 |
| 2007/0192133 A1 | 8/2007 | Morgan | |
| 2009/0189972 A1* | 7/2009 | Harris | A61B 5/444 348/14.08 |
| 2009/0311655 A1* | 12/2009 | Karkanias | G09B 5/065 434/262 |
| 2011/0161112 A1* | 6/2011 | Keefe | G16H 40/67 705/3 |
| 2012/0209314 A1* | 8/2012 | Weir | B25J 9/1694 606/205 |
| 2013/0287265 A1 | 10/2013 | Nepomniachtchi et al. | |
| 2014/0267582 A1* | 9/2014 | Beutter | H04N 7/147 348/14.12 |
| 2014/0297331 A1 | 10/2014 | Vazquez et al. | |
| 2015/0088547 A1 | 3/2015 | Balram et al. | |
| 2015/0356255 A1 | 12/2015 | Simpson et al. | |
| 2016/0103810 A1 | 4/2016 | Hanning | |
| 2016/0196400 A1 | 7/2016 | Hanning et al. | |
| 2016/0379504 A1 | 12/2016 | Bailey et al. | |

OTHER PUBLICATIONS

Paramasivan et al., U.S. Office Action dated Oct. 3, 2019, directed to U.S. Appl. No. 15/592,608; 15 pages.

* cited by examiner

EFFICIENT SURGICAL CENTER WORKFLOW PROCEDURES

CROSS-REFERENCE TO RELATED APPLICATIONS

This application is a divisional of U.S. patent application Ser. No. 15/592,608, filed May 11, 2017, which claims the benefit of U.S. Provisional Application No. 62/337,602, filed May 17, 2016, the entire contents of each of which are incorporated by reference herein.

FIELD OF THE INVENTION

The present invention relates to patient processing in a medical or surgical center, and in particular to efficient surgical center workflow procedures.

BACKGROUND OF THE INVENTION

Presently, the process for patient check-in, processing, scheduling for and performing a surgical process can be very time consuming and there are many times when errors in obtaining and recording patient information can be committed.

Typically, during patient check-in for a surgical procedure, the patient writes personal information on a paper chart. An admission professional at the surgical location receives the paper chart with the personal information filled in and obtains the patient's record. At large surgical centers and hospitals, the patient's record is maintained on a computer database and once the patient is checked-in using the paper chart, hospital systems such as hospital workflow systems, radiology information system (RIS)/hospital information system (HIS) and/or patient management systems can be accessed to create a surgical schedule for the patient. The surgical schedule allocates physical resources (e.g., particular operating rooms and equipment) and personnel resources (e.g., nurses) for the surgical procedure for the patient for specific times and creates alerts that the patient has checked into the system. A wristband for the patient can then be printed from information already stored in the hospital systems.

However, in small surgical centers that are not attached to large hospitals, but instead work with small clinics, there typically is no information system tie between the small clinics and the small surgical centers. At the isolated small clinics and surgical centers, the check-in procedure includes having the admission professional find a surgical record associated with the patient by comparing the hand written information with a pile of written surgical request forms (e.g., connected by staples or paper clips). The admission professional then creates a wristband for the patient by manually typing patient information into a wristband creation system and prints out the wristband. The admission professional can also manually create a surgical schedule for the patient. Such a system of admitting a patient is prone to user error and mistakes.

Once the patient is in the operating room, the patient is verified by a view of a wristband on the patient to ensure that the patient is correct. While the wristband may include a unique identifier that identifies the patient (e.g., a barcode), systems in the operating room that are not connected to the hospital workflow systems, RIS/HIS information systems or patient management systems are not able to obtain patient information from the unique identifier on the patient wristband. Typically, information is entered into systems in the operating room manually off of a printed scheduling sheet (from a scheduling system), from the wristband or from a patient chart that is transported into the operating room with the patient. The patient information can sometimes be pulled from a PACS using DICOM Modality Worklist functionality (which is designed for radiology systems) from information read from the wristband, but such a method typically can only be used when the patient has had a prior radiology exam and can be prone to errors (e.g., when the identification for the patient in the DICOM Modality Worklist is different than the identification on the wristband). It is contemplated that the systems could be tied in to the hospitals EMR/PMS systems to retrieve patient information, but such set up is rarely implemented because of a lack of systems in an operating room that interact with scheduling workflow systems.

For the procedure in the operating room, the record of the patient (including charts and history) can be reviewed from the memory of the surgeon and/or outside of the operating room prior to the surgery. An uneditable safe surgical checklist (e.g., a paper copy that is read during the surgery) can be conducted and saved to the patient record to ensure that the surgery is conducted properly on the proper person.

Privacy in medical facilities is very important to patients along with being legally mandated by the Health Insurance Portability and Accountability Act of 1996 in some situations. In many medical facilities, cameras capture images of rooms and communication is made using teleconferencing, video conferencing and video broadcasts. There is a desire to ensure that privacy is maintained during teleconferencing, video conferencing and video broadcasts. One method of ensuring privacy is disclosed in U.S. Pat. No. 9,258,522 entitled PRIVACY SETTING FOR MEDICAL COMMUNICATIONS SYSTEMS, the entire contents of which are hereby incorporated herein by reference.

A fast, easy and reliable method of arranging the medical or surgical devices in a medical care area is desired.

SUMMARY OF THE INVENTION

The present invention, according to various aspects, is directed to providing methods for efficiently processing surgical center workflow procedures. The methods include using optical character recognition for easing an admission process, entering patient information into operating room devices, using a wearable code to obtain a patient record, obtaining a patient record including a safe surgical checklist for review during a surgical procedure, providing a visual indication of information flow out of a medical care area and easily recording information on a whiteboard in the medical care area.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

For purposes of description herein, it is to be understood that the invention may assume various alternatives, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Aspects of the present disclosure are drawn to providing systems and methods for increasing efficiencies and accuracy during preparation for and conducting surgical procedures. The increasing efficiencies and accuracy can take place during admission of a patient to a medical or surgical facility, during admission of the patient into an operating theater, and during and after a medical or surgical procedure.

Admission

Figure 1:
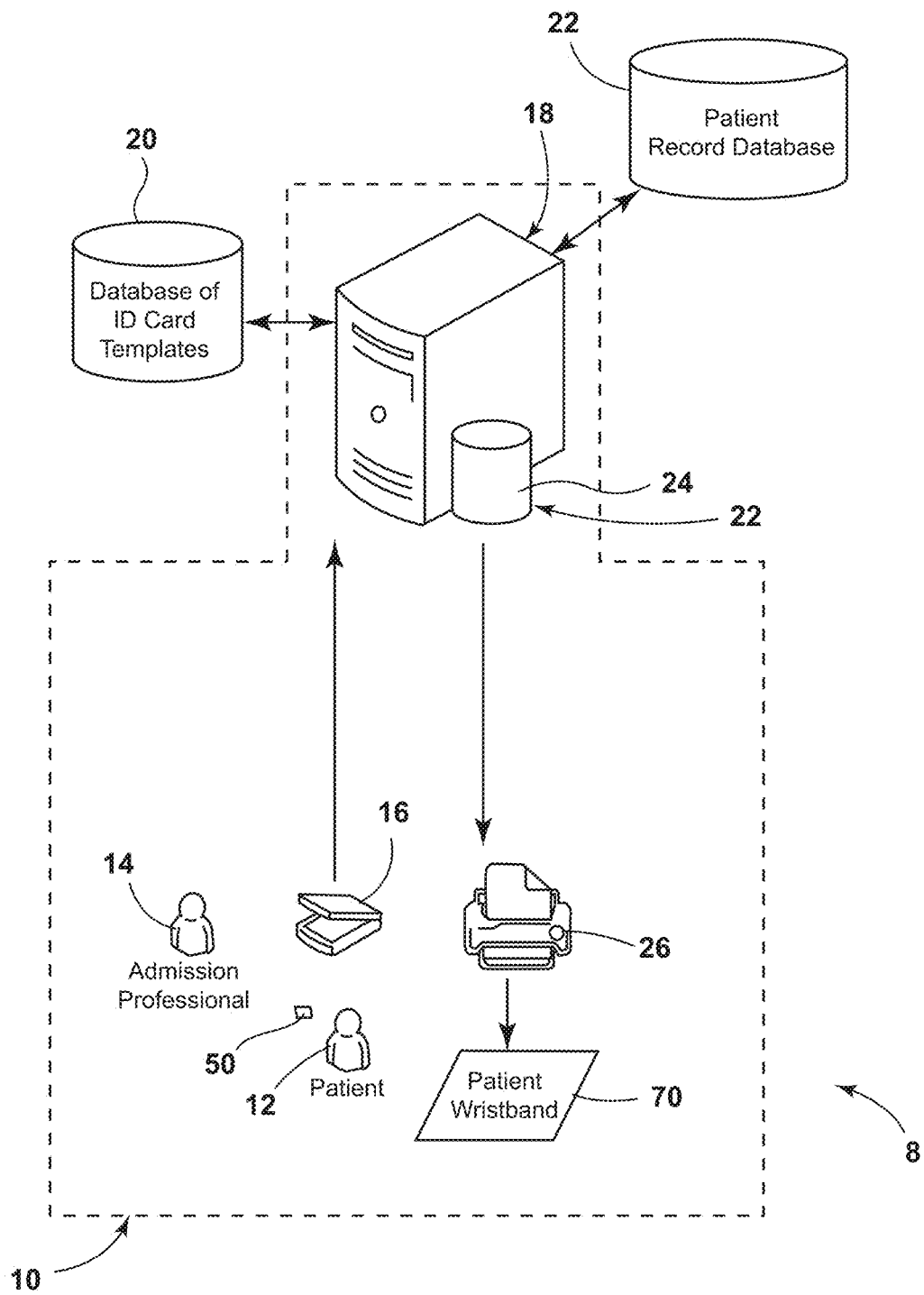
FIG. 1 is a schematic view of an admissions area of a medical or surgical center that employs a method of the present invention.
Figure 2:
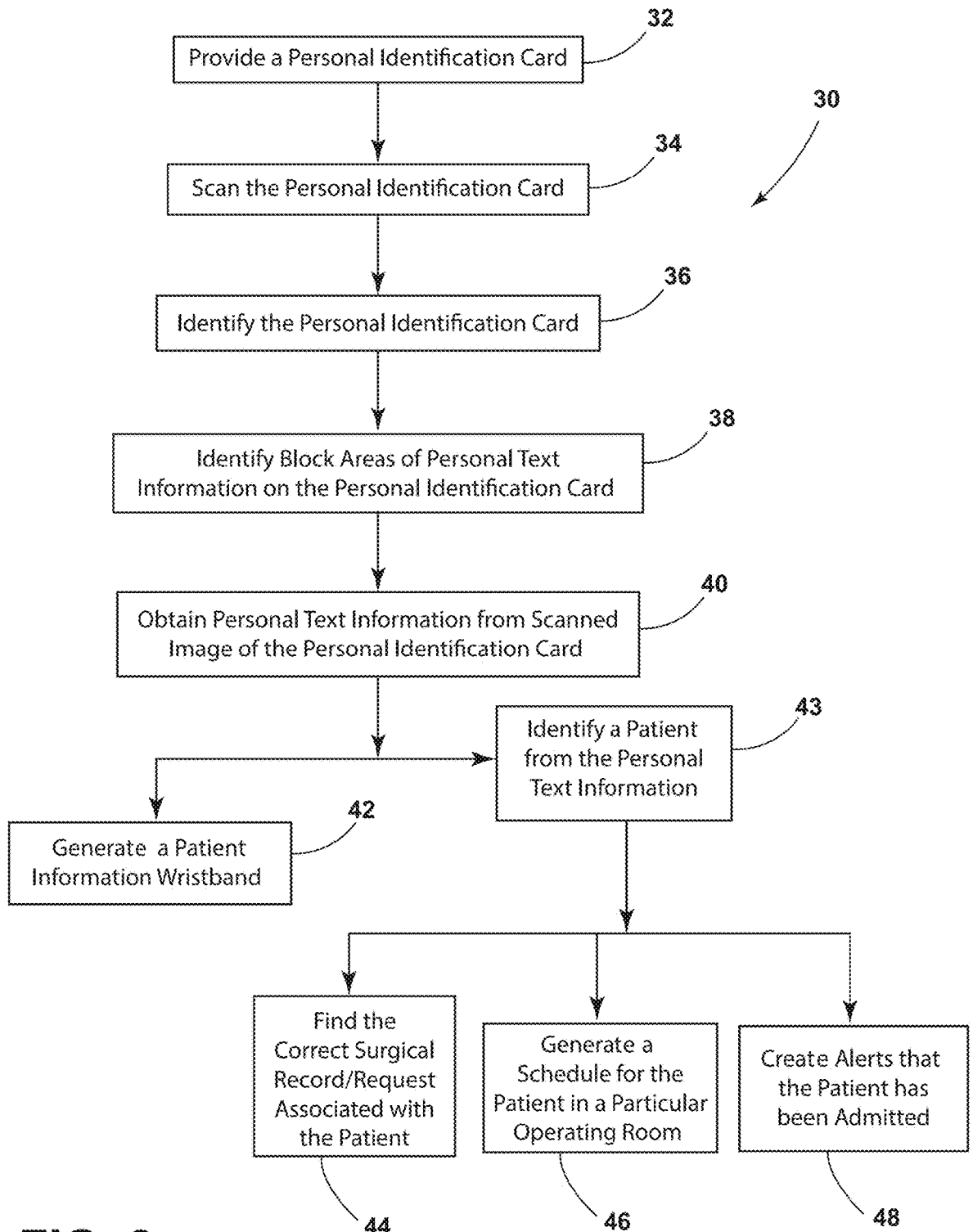
FIG. 2 illustrates an admission process of the present invention.
Figure 3:
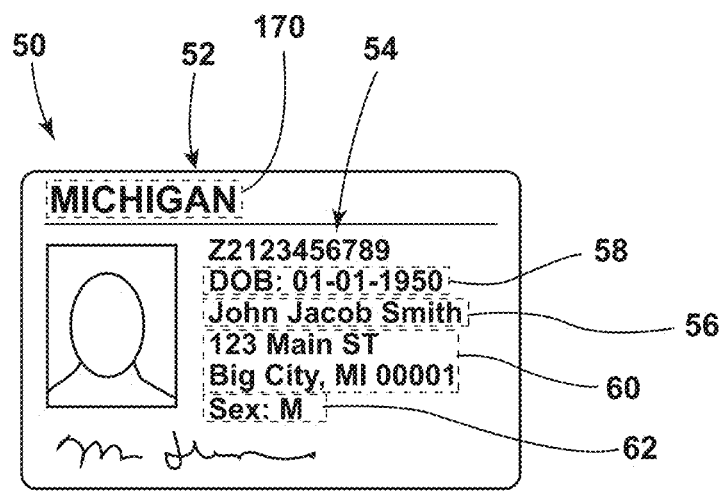
FIG. 3 illustrates a sample personal identification card used in the admission process of the present invention.

FIG. 1 illustrates schematically an admission area 10 of a medical or surgical center 8. In the admission area 10, a patient 12 engages with an admission professional 14 during an admission process 30 as outlined in FIG. 2. In a first step of the admission process 30, the patient 12 provides the admission professional 14 with a personal identification card 50 at step 32. The personal identification card 50 can be any card that identifies the patient 12. For example, the personal identification card 50 can be a state issued driver's license 52 as illustrated in FIG. 3, an insurance card of the patient 12, a military identification card of the patient 12, a state issued identification card or any other card or piece of paper that identifies the patient 12. The next step of the admission process 30 is to scan the personal identification card 50 with a scanner 16 at step 34. The scanner 16 can be a flatbed scanner (as illustrated), a roller scanner, a digital camera or any other device used to obtain an image of the personal identification card 50.

In the illustrated example, after the personal identification card 50 is scanned at step 34, the personal identification card 50 is identified at step 36. As illustrated in FIG. 1, the medical or surgical center 8 includes a computer system 18 having an application server in the admission area 10 that communicates with the scanner 16 (wired or wirelessly) to assist in identifying the personal identification card 50 at step 36. The computer system 18 can have a motherboard that includes one or more processors or other similar control devices as well as one or more memory devices. The processor controls the overall operation of the computer system 18 and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices.

The illustrated computer system 18 has access to a database of identification card templates 20. The database of identification card templates 20 can be located in the local memory device of the computer system 18 or the database of identification card templates 20 can be accessed from cloud storage or from any other storage system that communicates with the computer system 18 (e.g, via the internet). The database of identification card templates 20 includes a list of types of personal identification cards 50 entered therein (possibly including different varieties of the same type of card (e.g., when the card changes over time (e.g, a driver's license for several different issuance years as driver's licenses can change over time))). The admission professional 14 can access a web application on the computer system 18 to select the appropriate type of personal identification card 50 at step 36. For example, if the personal identification card 50 is a state of Michigan driver's license issued in 2010, the admission professional 14 will select the state of Michigan driver's license issued in 2010 using the web application on the computer system 18. It is also contemplated that the application server could include software (e.g., optical character recognition software) that can identify the type of identification card 50 (e.g., when the personal identification card 50 states that it is a driver's license of a particular state along with stating the date of issuance thereof) or that can determine the type of identification card 50 based on the configuration of the identification card 50 to be able to automatically select the appropriate type of personal identification card 50 from the database of identification card templates 20 at step 36.

Once the appropriate type of personal identification card 50 is selected at step 36, the computer system 18 will access the database of identification card templates 20 to identify block areas of personal text information 54 on the personal identification card 50 at step 38. The block areas of personal text information 54 define areas on the particular personal identification card 50 where particular personal text information 54 is located. For example, the block areas can include a patient name block area 56, a date of birth block area 58, an address block area 60, and a gender block area 62. The block areas can include any areas of information on the personal identification card 50 related to the patient 12.

In the illustrated example, after the block areas of personal text information 54 on the personal identification card 50 are identified at step 38, at least some of personal text information 54 on the personal identification card 50 is obtained from the scanned image at step 40. As illustrated in FIG. 3, the personal text information 54 can include the name of the patient taken from the patient name block area 56, a date of birth of the patient taken from the date of birth block area 58, an address of the patient taken from the address block area 60, and a gender of the patient taken from the gender block area 62. The personal text information 54 can include any of the information on the personal identification card 50 related to the patient 12. The personal text information 54 on the personal identification card 50 is obtained from the scanned image of the personal identification card 50 using image processing software and algorithms including optical character recognition, image normalization (e.g., using histogram equalization and/or color removal), feature extractions (e.g., line segment and edge detection) and/or pattern classification as is well known to those skilled in the art. Because of the information in the database of identification card templates 20, the personal text information 54 can be properly identified from the personal identification card 50 and saved in a record associated with the patient 12. It is contemplated that the personal text information 54 can be stored on a remote or external patient record database 22 communicating with the computer system 18 and/or on a local database 24 (permanently or temporarily) of the computer system 18.

Once the personal text information 54 is obtained from the scanned image at step 40, a patient information wristband 70 (see FIG. 4) can be generated at step 42. The patient information wristband 70 can be generated by printing the personal text information 54 on a blank patient wristband using a printer 26. The patient information wristband 70 can have the patient's surname printed in a patient surname area 72, the patient's given name printed in a patient given name area 74, the patient's date of birth printed in a patient date of birth area 76, the patient's gender printed in a patient gender area 78, or any other information obtained from the personal text information 54 on the personal identification card 50. The patient information wristband 70 can also have the age of the patient as calculated from the date of birth obtained from the personal identification card 50 printed in a patient age area 80. The patient information wristband 70 can further have additional patient information printed thereon, such as a patient ID number in a patient ID number area 82, the patient's doctor's name in a patient's doctor's name area 84, a barcode unique to the patient in a barcode area 86, and/or a QR code unique to the patient in a QR code area 88. It is contemplated that only some of the patient information outlined above and/or any other relevant information can be printed on the patient information wristband 70 (e.g., only patient name and patient ID number).

The illustrated admission process 30 can also include identifying the patient 12 from the personal text information 54 at step 43 and finding the correct surgical record/request associated with the patient 12 at step 44. The step 44 of finding the correct surgical record/request associated with the patient 12 can include matching the identification information (e.g., name) of the patient with a paper surgical record/request stored in the admission area 10, manually matching the identification information (e.g., name) of the patient with electronic surgical records/requests transmitted to the medical or surgical center 8 (or created at the medical or surgical center 8 on a previous date), or automatically matching the identification information (e.g., name) of the patient 12 with electronic surgical records/requests transmitted to the medical or surgical center 8 (or created at the medical or surgical center 8 on a previous date). The surgical records/requests can be stored on the computer system 18 or can be accessed by the computer system 18 (e.g., via an external storage system such as a remote database or a cloud storage system). At this point, the admission professional 14 or other medical professional can confirm/verify the identity of the patient 12 (including a visual verification of the patient 12 if there is a picture of the patient 12 on the personal identification card 50) along with correctly correlating the patient identification with a surgical record/request.

Once the patient 12 has been identified during step 43 of the admission process 30, the illustrated admission process 30 can also include generating a schedule for the patient 12 in a particular operating room at step 46 and/or creating alerts that the patient 12 has been admitted at step 48. The surgical schedule generated at step 46 allocates physical resources (e.g., particular operating rooms and equipment) and personnel resources (e.g., nurses) for the surgical procedure for the patient 12 for specific times. The alerts created at step 48 can include sending texts, emails and/or other messages to portable devices (e.g., cellular phones) carried by surgical personnel (e.g., nurses and doctors) or other devices (e.g., desktop and/or laptop computers) that the patient 12 has been admitted and will be ready for surgery. The alerts created at step 48 can also inform personnel at the medical or surgical center 8 to move appropriate resources (e.g., surgical equipment) to proper locations in anticipation of the medical or surgical procedure to be performed on the patient 12. Once the patient 12 has been identified during step 43 of the admission process 30, the illustrated admission process 30 can further include additional steps that will facilitate and/or expedite the procedure (e.g., printing out or creating needed forms with the relevant information thereon obtained from the personal text information 54 on the personal identification card 50 or obtained from a database of patient information accessed by matching a portion of the patient information in the database of patient information with the personal text information 54 on the personal identification card 50). All the above steps (including steps 46 and 48) can happen automatically under control of the computer system 18 using processing and communication systems well known to those skilled in the art.

Medical or Surgical Procedures Using Devices not Connected to a Network

Figure 5:
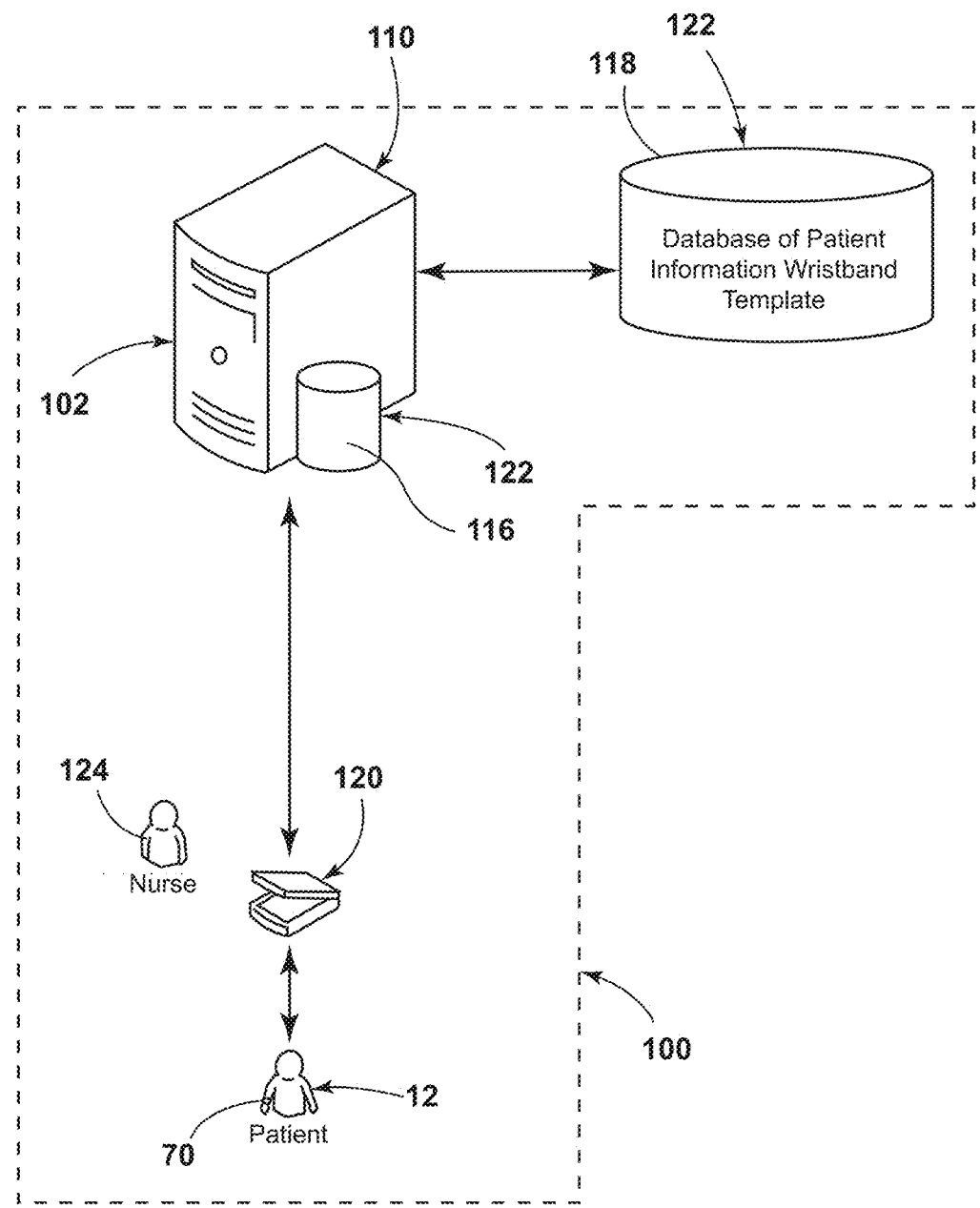
FIG. 5 illustrates a schematic view of a medical care area that employs a method of the present invention.
Figure 6:
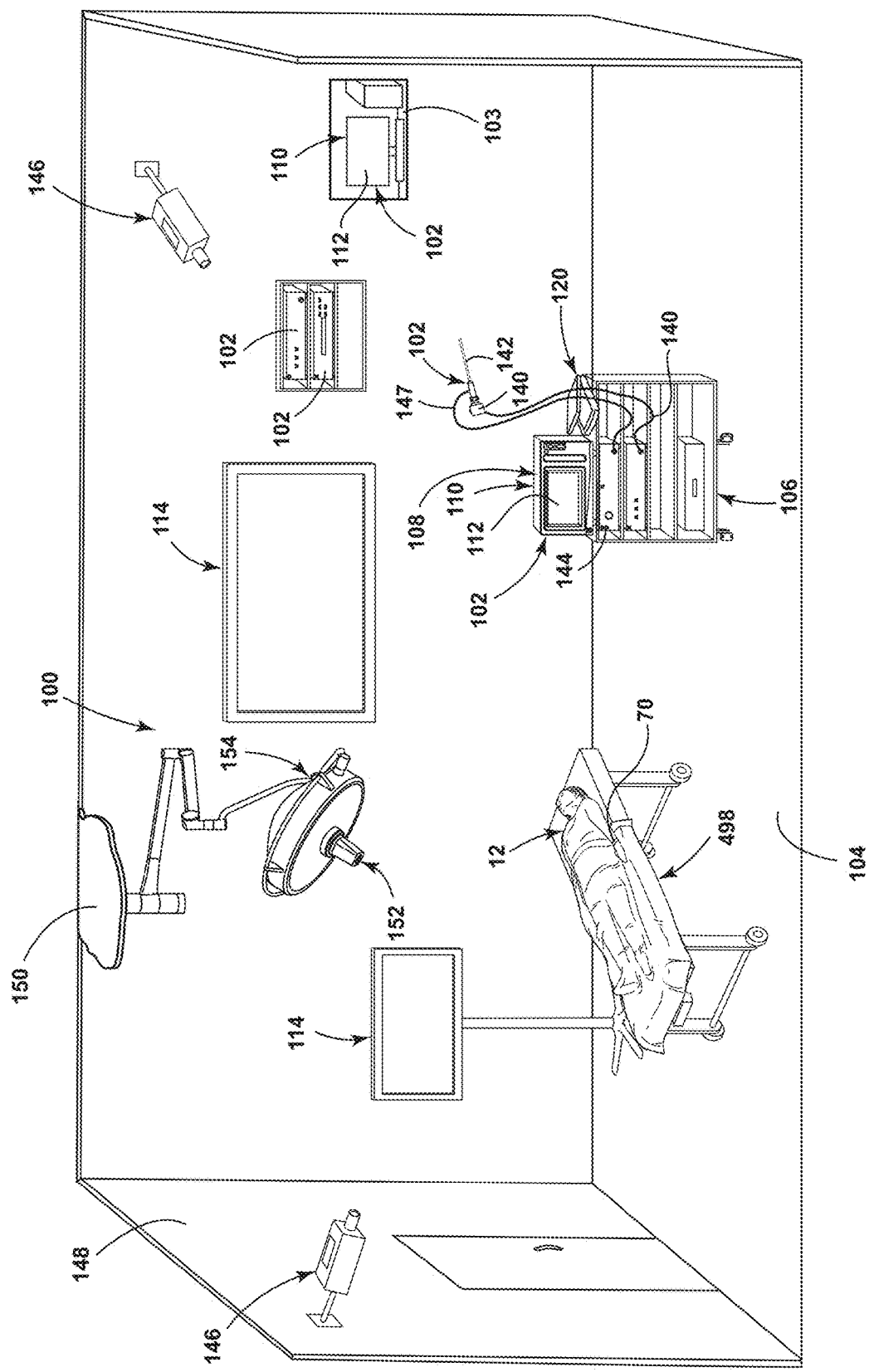
FIG. 6 is a perspective view of an operating room illustrating medical devices used in a method of the present invention.
Figure 7:
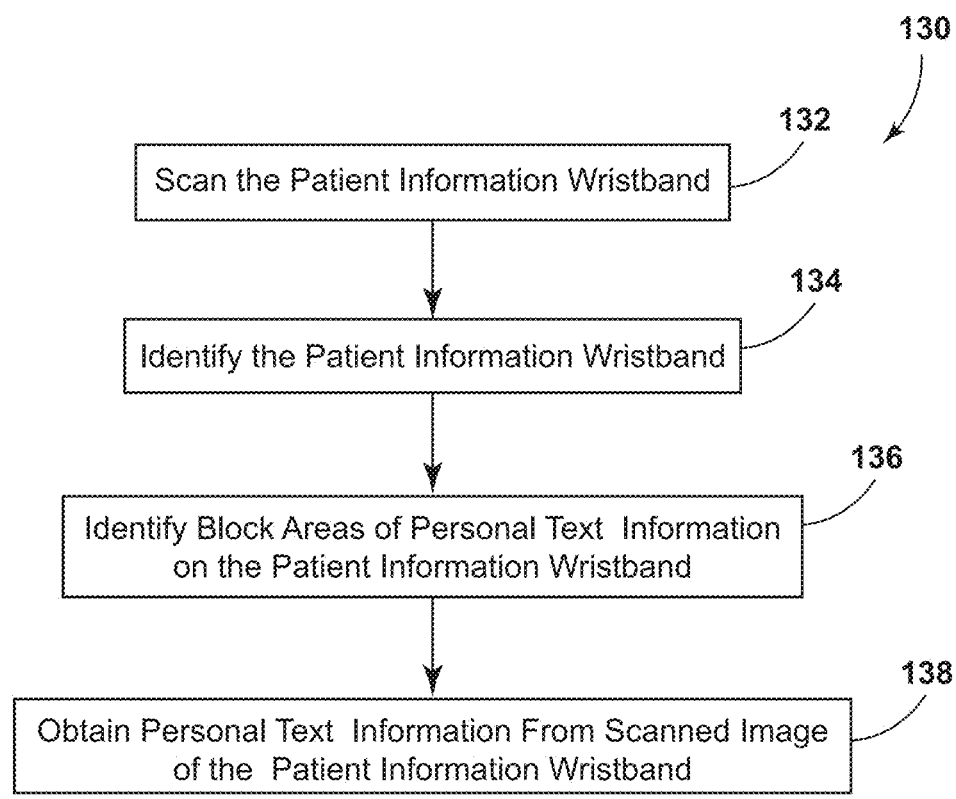
FIG. 7 illustrates a process of easily inputting the personal text information of a patient into the medical devices of the present invention.

After the patient 12 has been admitted to the medical or surgical center 8, the patient 12 will eventually proceed to a medical care area 100 (for example on a patient surgical table 498), which is illustrated schematically in FIG. 5 and as an operating room in FIG. 6. The medical care area 100 includes at least one medical device 102 to assist in performing a medical or surgical procedure and/or for record keeping purposes. In the illustrated example, the medical device 102 is not connected to any network at the medical or surgical center 8 that would allow the medical device 102 to receive any information related to the patient 12 that is to have the medical or surgical procedure performed thereon within the medical care area 100. An aspect of the present invention is to provide a method 130 (FIG. 7) of easily inputting the personal text information 54 of the patient 12 into the medical device 102 for use with information/images saved onto the medical device 102, for display with information/images from the medical device 102 and/or for sending to further medical devices 102.

The medical device 102 located within the medical care area 100 of the medical or surgical center 8 in the present aspect of the present invention can include any device that is capable of saving information related to the patient 12, but that is not presently connected to a network that includes records of the patient in such a manner that records or information related to the patient 12 is readily available. However, it is contemplated that medical devices 102 that are connected to a network such that the medical devices 102 could access records of the patient 12 in such a manner that records or information related to the patient could be obtained could also employ the method 130 of easily inputting personal text information 54 of the patient 12 into the medical device 102.

In the illustrated example, the medical device 102 includes a computer system 110 having an application server thereon (e.g., a desktop computer 110 (as shown in FIGS. 5 and 6), a laptop computer or incorporated into a medical system as shown in FIG. 6 and as described in more detail below). The computer system 110 can have a motherboard that includes one or more processors or other similar control devices as well as one or more memory devices. The processor controls the overall operation of the computer system 110 and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices. The personal text information 54 of the patient 12 can be inputted into the computer system 110 for use with the computer system 110 (e.g., for making an operative note during the medical or surgical procedure on the patient 12 in the medical care area 100) and/or the computer system 110 can transmit the personal text information 54 of the patient 12 (via either a wired connection or wirelessly) to another medical device 102 within the medical care area 100.

In a first step of the method 130 of easily inputting personal text information 54 of the patient 12 into the medical device 102, the patient information wristband 70 on the patient 12 is scanned with a scanner 120 at step 132. The scanner 120 can be a flatbed scanner (as illustrated in FIGS. 5 and 6), a roller scanner, a digital camera or any other device used to obtain an image of the patient information wristband 70. The scanner 120 can take a single image of the patient information wristband 70 (e.g., a panoramic image) or can take multiple images to obtain a clear image of all of the personal text information 54 on the patient information wristband 70.

In the illustrated example, after the patient information wristband 70 is scanned at step 132, the patient information wristband 70 is identified at step 134. As illustrated in FIG. 5, the computer system 110 communicates with the scanner 120 (wired or wirelessly) to assist in identifying the patient information wristband 70. The computer system 110 has access to a database of patient information wristband templates 122. The database of patient information wristband templates 122 can be located in the local memory device 116 of the computer system 110 or the database of patient information wristband templates 122 can be accessed from cloud storage or from any other storage system 118 that communicates with the computer system 110 (e.g, via the internet). The database of patient information wristband templates 122 includes a list of types of patient information wristbands 70 entered therein. A nurse 124 or other personnel in the medical care area 100 can access a web application on the computer system 110 to select the appropriate type of patient information wristband 70 that matches the actual patient information wristband 70 at step 134. It is also contemplated that the computer system 110 could include software (e.g., optical character recognition software that can read the type of patient information wristband 70 (e.g., stated on the patient information wristband 70) or that can determine the type of patient information wristband 70 based on the configuration of the patient information wristband 70) to be able to automatically select the appropriate type of patient information wristband 70 from the database of patient information wristband templates 122 at step 134. It is further contemplated that the barcode or the QR code on the patient information wristband 70 could identify the type of patient information wristband 70.

Once the appropriate type of patient information wristband 70 is selected at step 134, the computer system 110 will access the database of patient information wristband templates 122 to identify block areas of personal text information 54 on the patient information wristband 70 at step 136. The block areas of personal text information 54 define areas on the patient information wristband 70 where particular personal text information 54 is located. For example, the block areas (see FIG. 4) can include the patient surname area 72, the patient given name area 74, the patient date of birth area 76, the patient gender area 78, the patient age area 80, the patient ID number area 82, the patient's doctor's name area 84, the barcode area 86, and/or the QR code area 88 as outlined above or any other area including relevant information.

Figure 4:
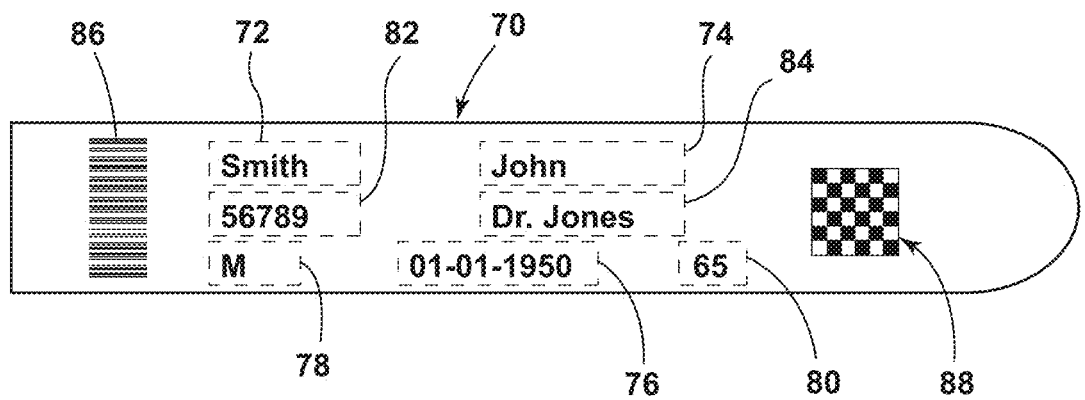
FIG. 4 illustrates a patient information wristband for use with the present invention.

In the illustrated example, after the block areas of personal text information 54 on the patient information wristband 70 are identified at step 136, at least some of the personal text information 54 on the patient information wristband 70 is obtained from the scanned image at step 138. As illustrated in FIG. 4, the personal text information 54 can include the surname of the patient 12 taken from the patient surname area 72, the given name of the patient 12 taken from the patient given name area 74, the date of birth of the patient 12 taken from patient date of birth area 76, the gender of the patient 12 taken from the patient gender area 78, the age of the patient 12 taken from the patient age area 80, the ID number of the patient 12 taken from the patient ID number area 82, the name of the doctor of the patient 12 taken from the patient's doctor's name area 84, the barcode identifying the patient 12 taken from the barcode area 86, and/or the QR code identifying the patient 12 taken from the QR code area 88 as outlined above or any other area including relevant information. The personal text information 54 can include any of the information on the patient information wristband 70 related to the patient 12. The personal text information 54 on the patient information wristband 70 is obtained from the scanned image of the patient information wristband 70 using image processing software and algorithms including optical character recognition, image normalization (e.g., using histogram equalization and/or color removal), feature extractions (e.g., line segment and edge detection) and/or pattern classification as is well known to those skilled in the art. Because of the information in the database of patient information wristband templates 122, the personal text information 54 can be properly identified from the patient information wristband 70 and saved in a record associated with the patient 12.

Once the personal text information 54 is obtained from the scanned image at step 138, the personal text information 54 can be saved with information/images saved onto the medical device 102 (either in a record associated with the information/images or onto the information/images), displayed with information/images from the medical device 102 and/or sent to further medical devices 102. For example, the personal text information 54 can be used to populate appropriate fields in a surgical note created using the process set forth in U.S. patent application Ser. No. 14/853,289 entitled INTRA-SURGICAL DOCUMENTATION SYSTEM. The personal text information 54 can also be used to identify the surgeon and/or surgical procedure to obtain preferences for arranging the medical care area 100 as set forth in U.S. Patent Application No. 62/183,995 entitled METHOD AND SYSTEM FOR SURGICAL INSTRUMENTATION SETUP AND USER PREFERENCES or in U.S. patent application Ser. No. 14/982,636 entitled METHOD OF CONFIGURING DEVICES IN AN OPERATING THEATER, the entire contents of which are hereby incorporated herein by reference.

The illustrated medical devices 102 can be positioned in the medical care area 100 on a table (stationary or portable), on a floor 104, on a portable cart 106 and/or on shelving 103 in the medical care area 100. FIG. 6 illustrates two computer systems 110: a first computer system 110 in the form of a desktop computer on shelving 103 and a second computer system 110 incorporated into an image and video capture and recording device 108 on the portable cart 106. However, it is contemplated that the computer system 110 could be on the portable cart 106 (e.g., on the same cart 106 as the image and video capture and recording device 108 or on a separate cart). The illustrated image and video capture and recording device 108 is capable of recording images and videos and displaying images and videos. In an aspect of the present invention, the personal text information 54 of the patient 12 can be inputted into the image and video capture and recording device 108 for adding to the images and videos recorded and/or displayed by the image and video capture and recording device 108. The illustrated image and video capture and recording device 108 can include an internal hard drive for storing the captured images and videos. The image and video capture and recording device 108 can also display any captured or saved images (e.g., from the internal hard drive) on an associated touchscreen monitor 112 and/or an additional monitor 114 connected to the image and video capture and recording device 108 via either a wired connection or wirelessly. It is contemplated that the image and video capture and recording device 108 could obtain or create images of a patient during a medical or surgical procedure from a variety of sources (e.g., from video cameras, video cassette recorders, X-ray scanners (which convert X-ray films to digital files), digital X-ray acquisition apparatus, fluoroscopes, CT scanners, MRI scanners, ultrasound scanners, CCD devices, and other types of scanners (handheld or otherwise)). If connected to a network, the image and video capture and recording device 108 can also communicate with a picture archiving and communication system (PACS), as is well known to those skilled in the art, to save images and video in the PACS and for retrieving images and videos from the PACS. The illustrated image and video capture and recording device 108 is therefore capable of displaying images and videos on the touchscreen monitor 112 and/or on the additional monitor 114 captured live by cameras (e.g., a video camera 140 connected to an associated endoscope 142, which communicates with a camera control unit 144 via a fiber optic cable 147, with the camera control unit 144 communicating via wires or wirelessly with the image and video capture and recording device 108) and/or replayed from recorded images and videos. It is further contemplated that the image and video capture and recording device 108 can display images and videos on the touchscreen monitor 112 and/or on the additional monitor 114 captured live by a room camera 146 fixed to walls 148 or a ceiling 150 of the medical care area 100 (e.g., a room camera 146 as shown or a camera 152 in an overhead light 154).

Figure 8:
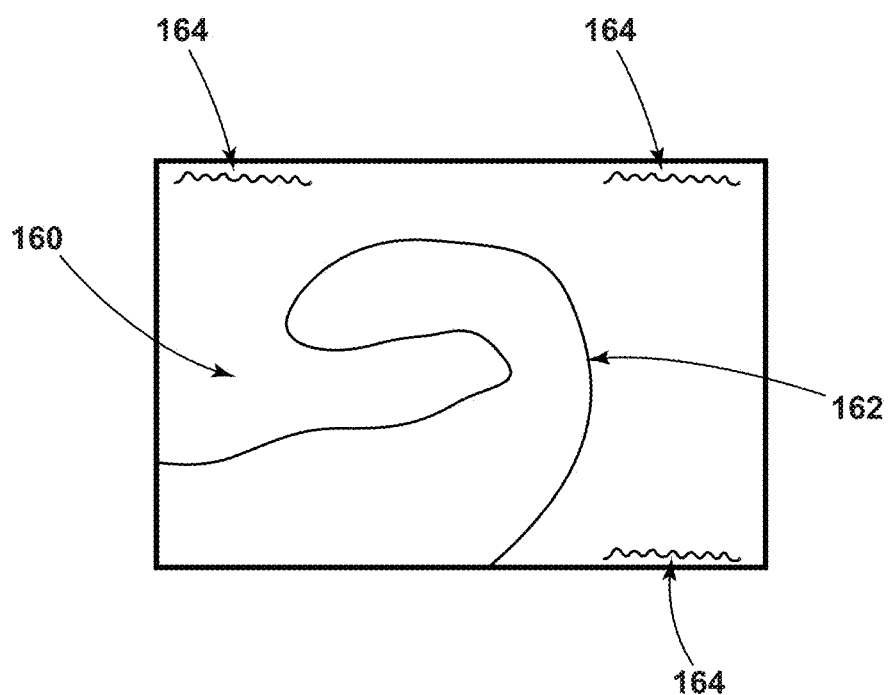
FIG. 8 is an image from the medical devices of the present invention.

FIG. 8 illustrates an image (e.g., from the image and video capture and recording device 108) being displayed on the touchscreen monitor 112 of the image and video capture and recording device 108 or on the additional monitor 114. FIG. 8 illustrates an image 160 from the image and video capture and recording device 108 (e.g., captured by the video camera 140 connected to the image and video capture and recording device 108), with the image 160 including a picture portion 162 and text portions 164. The text portions 164 can be adjacent to the picture portion 162 or superimposed onto the picture portion 162. It is further contemplated that the picture portion 162 can be a plurality of images (e.g., a live image side by side with a stored image). The text portions 164 can include any of the personal text information 54 as outlined above.

Saving Templates

The identification card templates can be saved to the database of identification card templates 20 using a web application 166 stored on the computer system 18. Likewise, the wristband templates can be saved to the database of patient information wristband templates 122 using the web application 166 stored on the computer system 110.

Figure 9:
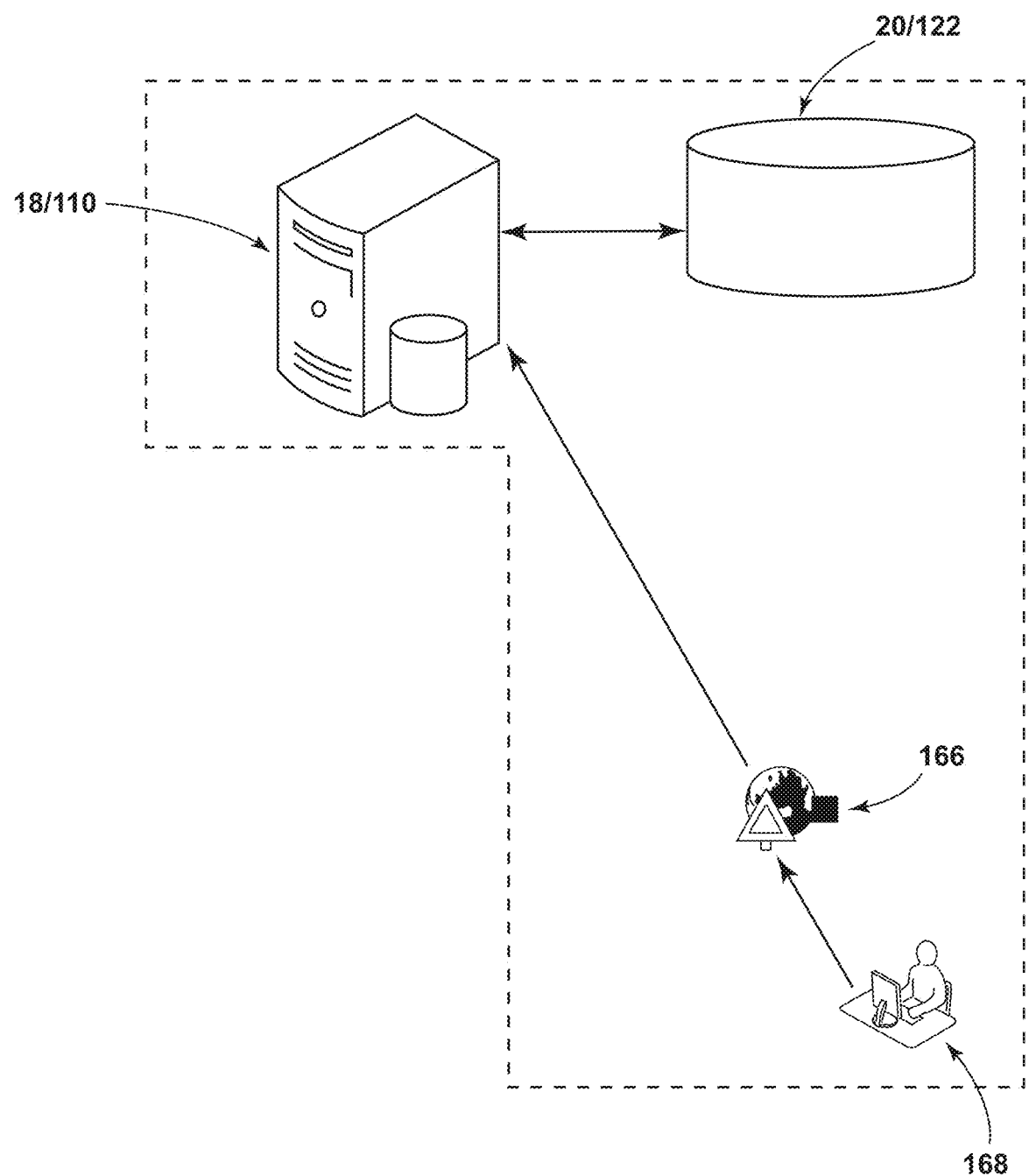
FIG. 9 illustrates a schematic view of a template entering area that employs a method of creating templates of the present invention.

FIG. 9 illustrates schematically a process for saving the identification card templates to the database of identification card templates 20 and the wristband templates to the database of patient information wristband templates 122. In order to save the identification card templates and the wristband templates, a data entry person 168 (at the medical center or at another location) accesses the web application 166. The web application 166 will have access to an image of a personal identification card 50 or a patient information wristband 70 for entry into the relevant database. The image of the personal identification card 50 or the patient information wristband 70 can be obtained by capturing an image of the personal identification card 50 or the patient information wristband 70 (e.g., by scanning). Alternatively, the personal identification card 50 or the patient information wristband 70, or a representation thereof, can be entered into the web application 166 in any other manner.

Once the personal identification card 50 or the patient information wristband 70, or a representation thereof, is entered into the web application 166, the data entry person 168 enters a name of the identification card or the wristband, or a representation thereof, into the web application 166. For example, if the state of Michigan driver's license of FIG. 3 is entered into the web application 166, the name of the personal identification card 50 will be associated with the state of Michigan driver's license. Therefore, the admission professional 14 can later access the web application 166 on the computer system 18 to select the appropriate type of personal identification card 50 at step 36, in this case, a state of Michigan driver's license. Alternatively, the web application 166 can be programmed to search the personal identification card 50 for an indication that the personal identification card 50 is a state of Michigan driver's license. For example, the web application 166 can be programmed to search a state identification block 170 and use OCR to determine if the word "MICHIGAN" is in the state identification block 170. If the word "MICHIGAN" is in the state identification block 170, the computer system 18 will know that the personal identification card 50 is a state of Michigan driver's license at step 36.

Along with having the data entry person 168 enter the location of the state identification block 170 and the word to search for in the state identification block 170, the data entry person 168 can enter the location and/or size of the block areas of personal text information 54 on the personal identification card 50 (e.g., the patient name block area 56, the date of birth block area 58, the address block area 60, and the gender block area 62). A mouse or other computer interface device can be used to locate and size the block areas of personal text information 54 on the personal identification card 50 or the patient information wristband 70, or the representation thereof. Moreover, a mouse (e.g., using a pull down menu) or other computer interface device (e.g., a keyboard) can be used to associate the block area with the particular type of personal text information 54 located within the particular block area. The same process described above for entering a state of Michigan driver's license into the database of identification card templates 20 can be used to enter any other personal identification card 50 into the database of identification card templates 20 and or entering patient information wristbands 70 into the database of patient information wristband templates 122. It is contemplated that the web application 166 can be hosted on the computer systems 18, 110 or that the web application 166 can be hosted on another computer system and that the data entered into the web application 166 can then be transferred to the database of identification card templates 20 and the database of patient information wristband templates 122 in any manner (e.g., using a portable memory device or access through an internet connection). It is further contemplated that the barcode and/or the QR code on the patient information wristband 70 can be saved to the database of patient information wristband templates 122 to inform the computer system 110 of the patient information wristband 70 being analyzed to allow the computer system 110 to know the block areas of text information 54 on the patient information wristband 70. While a particular manner of saving identification card templates to the database of identification card templates 20 and the wristband templates to the database of patient information wristband templates 122 is outlined above, it is contemplated that the identification card templates can be saved to the database of identification card templates 20 and the wristband templates can be saved to the database of patient information wristband templates 122 in any manner using any system.

Using a Wearable Code to Obtain a Patient Record

As outlined above, after the patient 12 has been admitted to the medical or surgical center 8, the patient 12 will eventually proceed to the medical care area 100. As also outlined above, the medical care area 100 includes medical devices 102 to assist in performing a medial or surgical procedure and/or for record keeping purposes. The patient information wristband 70 outlined above can be used to transfer personal text information 54 to the computer systems 110 and the medical devices 102. The barcode unique to the patient 12 and/or a QR code unique to the patient 12 on the patient information wristband 70 can also be used to obtain a patient record of the patient 12 for use with any of the computer systems 110 and/or medical devices 102 or to be displayed from any of the medical devices 102. The medical devices 102 that obtain the medical records as outlined in this paragraph can be connected to a network. It is contemplated that the patient information wristband 70 could include an RFID chip having a code stored therein that is unique to the patient 12 and that is read by an RFID chip reader connected to or part of the medical devices 102 (e.g., the image and video capture and recording device 108) instead of using a scanner for scanning the barcode unique to the patient 12 and/or a QR code unique to the patient 12. Moreover, it is contemplated that a camera interacting with the medical devices 102 (e.g., the image and video capture and recording device 108) could scan the face of the patient 12 and facial recognition software could be used to identify the patient 12.

Figure 10:
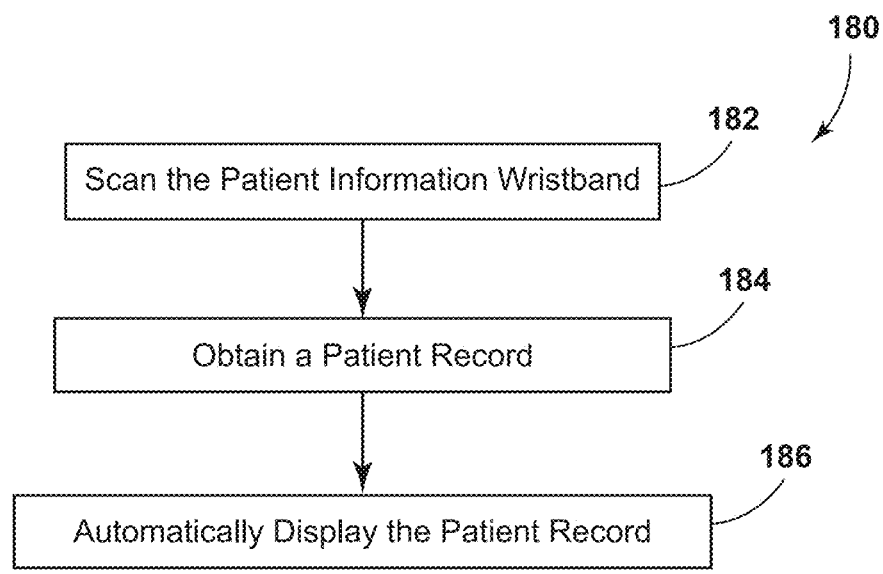
FIG. 10 illustrates a method of obtaining a patient record according to an aspect of the present invention.
Figure 11:
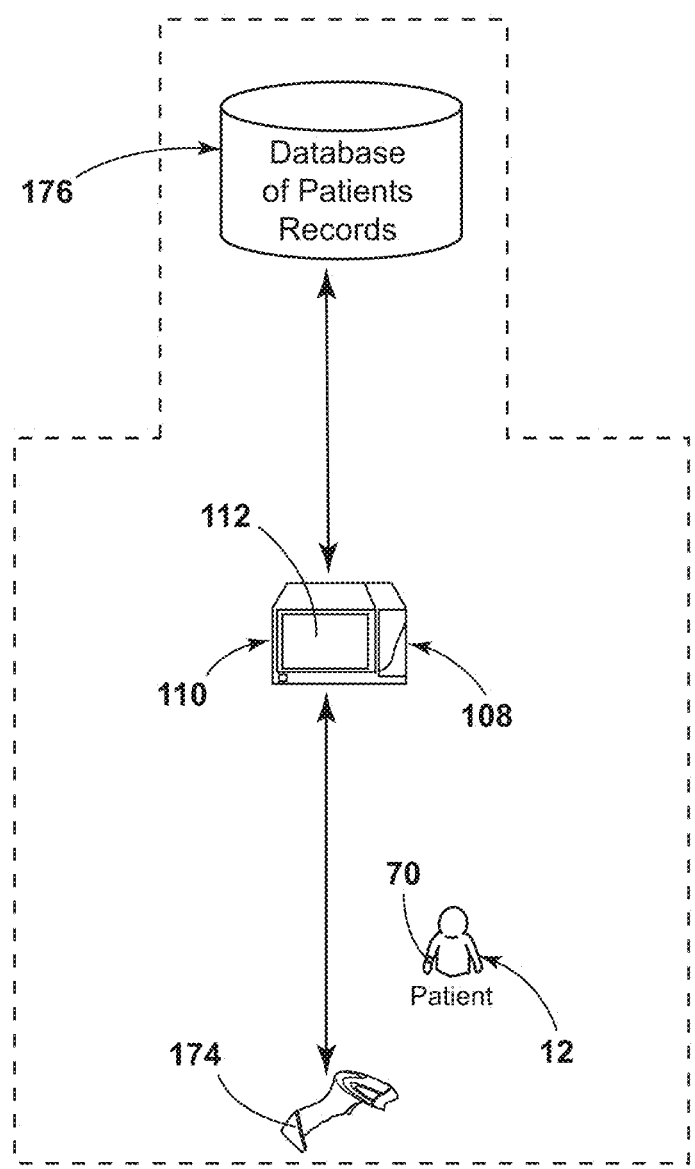
FIG. 11 illustrates a schematic view of a medical care area that employs a method of automatically obtaining a patient record of the present invention.

FIG. 10 illustrates a method 180 of obtaining a patient record. In a first step of the method 180 of obtaining a patient record, the patient information wristband 70 on the patient 12 is scanned with a code scanner 174 to identify the patient 12 at step 182. The code scanner 174 can be a barcode scanner (as illustrated in FIG. 11), a flatbed scanner, a QR code scanner, a roller scanner, a digital camera or any other device used to obtain a scan of the patient information wristband 70. Instead of a code scanner used in step 182, it is contemplated that an RFID scanner or a camera using facial recognition software could be used in step 182 to identify the patient 12. Thereafter, the computer system 110 (e.g., the image and video capture and recording device 108) connects to a database of patient records 176 to obtain the patient record at step 184. The database of patient records 176 can be queried from or use a Digital Imaging and Communications in Medicine (DICOM) Modality Worklist, Electronic Medical Records or any other Application Programming Interface that allows for the patient record to be obtained from the database of patient records 176. After the patient record is obtained at step 184, the patient record is automatically displayed for scheduling and/or case management at step 186. For example, after step 182 is performed manually, the computer system 110 will automatically perform step 184 of obtaining the patient record and then automatically perform step 186 and display the patient record on the touchscreen monitor 112 of the image and video capture and recording device 108.

Surgical Record and Checklist

Figure 12:
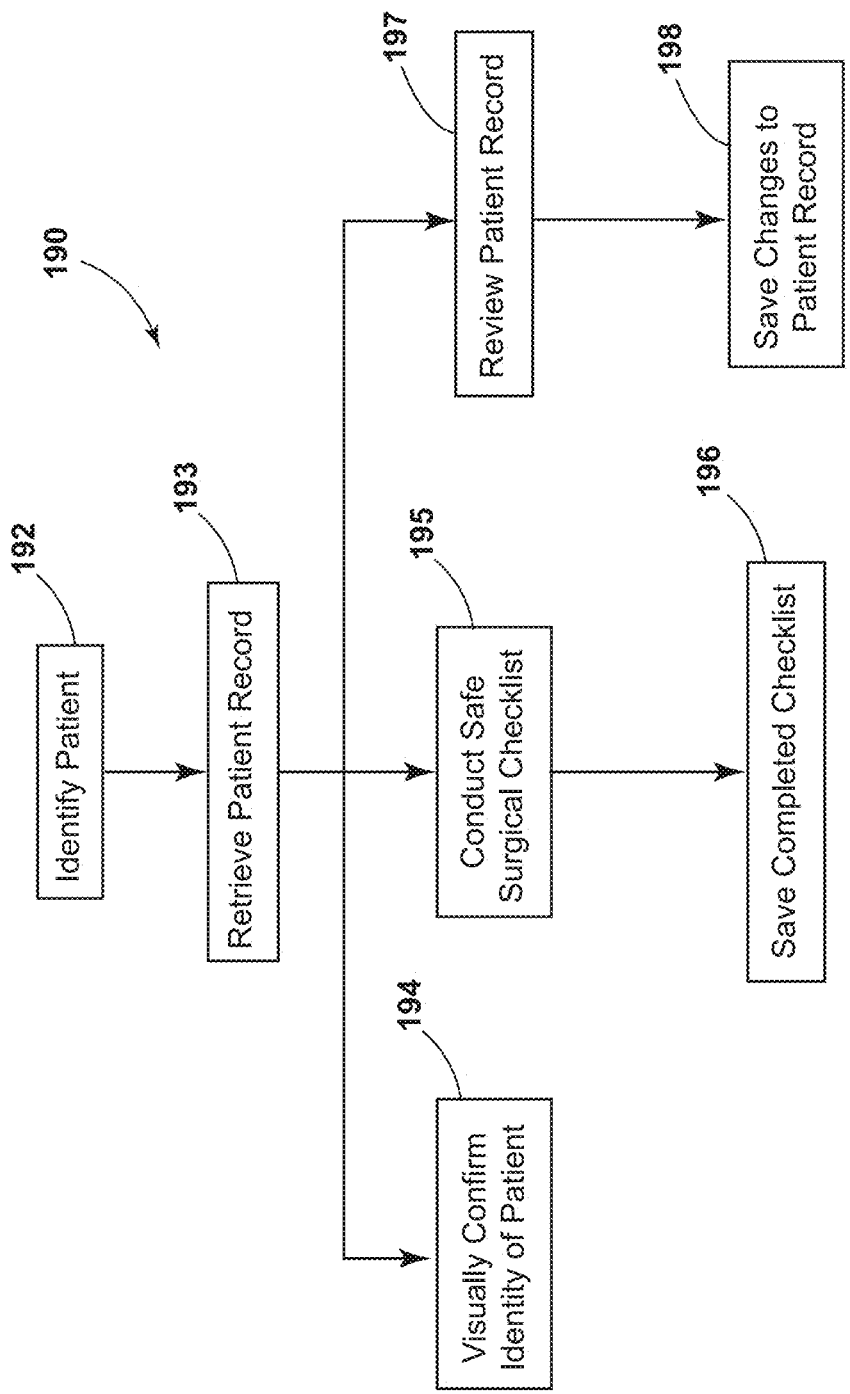
FIG. 12 illustrates a method of obtaining the patient record for use and review during the medical or surgical procedure according to an aspect of the present invention.
Figure 13:
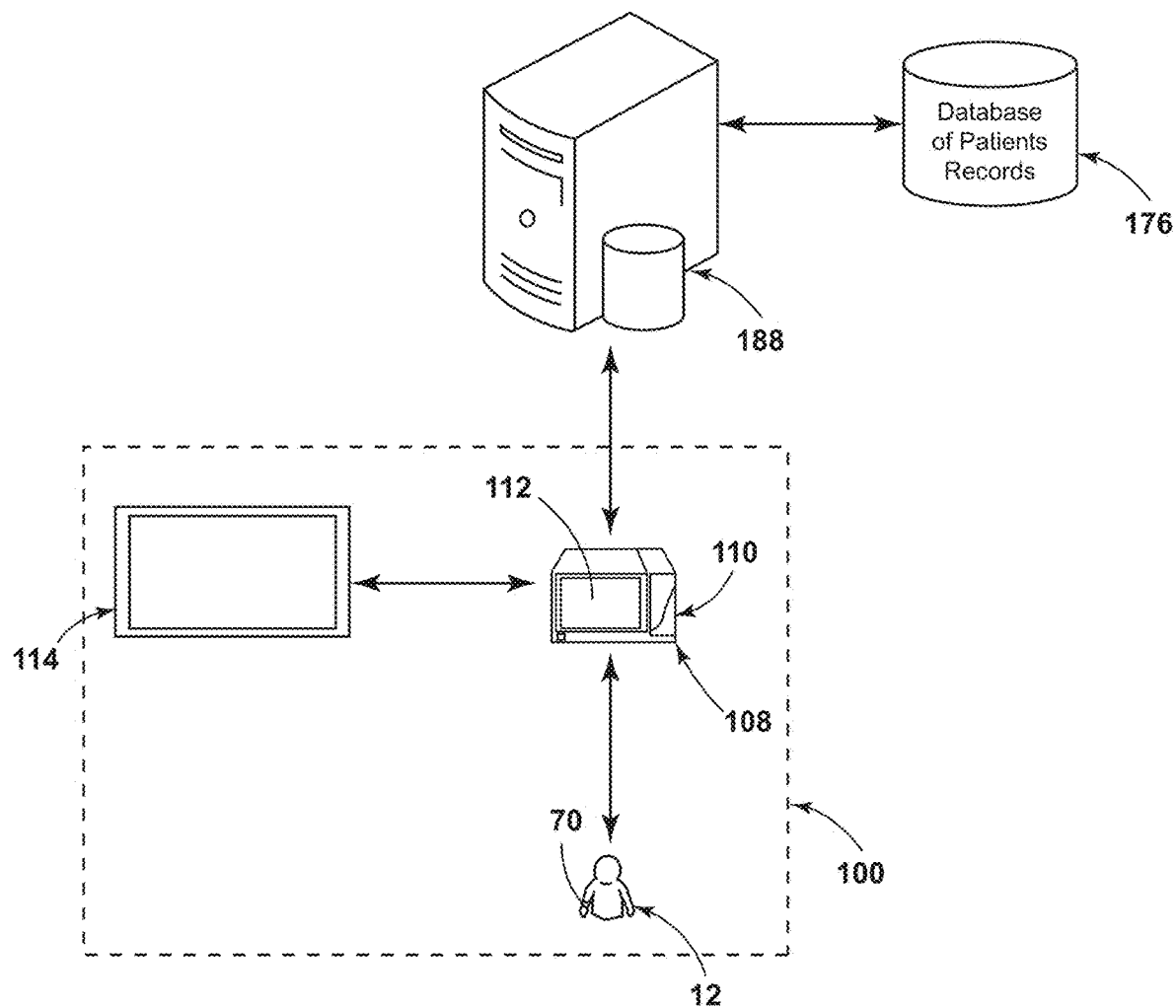
FIG. 13 illustrates a schematic view of a medical care area that employs the method of obtaining the patient record for use and review during the medical or surgical procedure of the present invention.

Another aspect of the present invention is to provide a method 190 of obtaining the patient record for use and review during the medical or surgical procedure (FIG. 12). In this aspect of the present invention as illustrated in FIG. 13, the computer system 110 and/or the medical device 102 (e.g., including the computer system 110 therein) located within the medical care area 100 of the medical or surgical center 8 is connected to a network that includes the patient records that are readily available.

A first step in the illustrated method 190 of obtaining the patient record for use and review during the medical or surgical procedure includes identifying the patient 12 at step 192. The patient 12 can be identified in any reliable manner. For example, the patient 12 can be identified using the patient information wristband 70 worn by the patient 12. For another example, the patient 12 can be identified in step 192 by using the method 130 of easily inputting personal text information 54 of the patient 12 into the medical device 102. Alternatively, the patient 12 can be identified using step 182 of the method 180 of obtaining the patient record as outlined above. It is further contemplated that the patient can be identified by manually inputting the patient information into the computer system 110 and/or the medical device 102 (e.g., typing the patient information into the computer system 110 and/or the medical device 102 or finding the patient's name using a pull down menu (e.g., using a DICOM Modality Worklist)). Moreover, the patient 12 can be identified using facial recognition or from an RFID chip worn by the patient 12 as outlined above.

It is also contemplated that the patient 12 can be identified by inputting the patient information into the computer system 110 and/or the medical device 102 using voice commands. If using voice commands, it is contemplated that the computer system 110 and/or the medical device 102 could include a voice control. For example, the image and video capture and recording device 108 could include a voice-responsive control system (VCS). The VCS can receive speech from a user (e.g., surgeon) to control functions of various components in the image and video capture and recording device 108. The VCS can be integrated into the image and video capture and recording device 108 or can be separate from, but connected to, the image and video capture and recording device 108. Therefore, certain functions of the image and video capture and recording device 108 may be controlled by voice commands using the VCS. Speech from a user can be input into the VCS through a microphone on a headset worn by the user or through a microphone located in the medical care area 100. The headset can be wired to the image and video capture and recording device 108 or can communicate wirelessly with the image and video capture and recording device 108 (e.g., using Bluetooth communication or WiFi communication). The VCS includes an automatic speech recognition (ASR) engine to recognize and generate control signals in response to the user's speech. An example of the image and video capture and recording device 108 with the VCS is disclosed in U.S. patent application Ser. No. 14/982,636 entitled METHOD OF CONFIGURING DEVICES IN AN OPERATING THEATER, the entire contents of which are hereby incorporated herein by reference.

Once the patient 12 is identified at step 192, the patient record can be retrieved by the computer system 110 and/or the medical device 102 from a remote location at step 193. As illustrated in FIG. 13, the patient record can be stored in the database of patient records 176 communicating with or part of an electronic medical record (EMR) 188 communicating with the computer system 110 and/or the medical device 102 (all wired or wireless). It is contemplated that the patient record could be stored in and retrievable from any other record keeping database in any manner (e.g., obtainable from a cloud storage system). Once the patient record is retrieved at step 193, the patient record can be locally saved on the computer system 110 and/or the medical device 102 to allow the surgeon and surgical team to view information in the patient record during surgery to review information before making critical decisions as discussed in more detail below.

After the patient record is retrieved at step 193, the patient record can be used in several different manners to assist in the medical or surgical procedure. For example, the patient record could be used to identify the patient 12. The patient record can include a picture of the patient 12. Therefore, after the patient record is retrieved at step 193, the picture of the patient 12 can be displayed by the computer system 110 and/or the medical device 102 (e.g, on the touchscreen monitor 112 of the image and video capture and recording device 108 and/or on the additional monitor 114). The identity of the patient 12 can then be visually confirmed at step 194. Facial recognition could also be used as outlined above to compare the picture of the patient 12 in the patient record with the actual image of the patient 12 to assist in conclusively identifying the patient 12.

In the illustrated example, the patient record retrieved in step 193 can also be used to retrieve a safe surgical checklist (which is a portion of the patient record) and to conduct the safe surgical checklist at step 195. The safe surgical checklist pertains to the particular medical or surgical procedure being performed by the surgeon and can include a checklist that the surgeon and/or other medical personnel can check before and during the medical or surgical procedure to ensure that the correct procedure is being performed on the correct person and at the correct site (e.g., by checking information to ensure that the correct patient 12 is to be operated on, checking to ensure that the correct procedure is performed, checking to ensure that the surgery is being performed on the correct area of the patient 12, etc.).

The safe surgical checklist can include a list of information that can be confirmed before the checklist can proceed. For example, the touchscreen monitor 112 of the image and video capture and recording device 108 can include items that need to be manually checked before the medical or surgical procedure can proceed. In this example, a first part of step 195 can include the step 194 of showing a picture of the patient 12 along with requiring a surgeon or medical personnel to touch a confirmation button on the touchscreen monitor 112 that the patient 12 is the same as the patient 12 shown in the picture of the medical record. Further parts of step 195 of conducting the safe surgical checklist can be used to establish that the correct type of procedure is being performed and can occur prior to critical points during the surgical or medical procedure such as prior to administration of anesthesia, prior to skin incision and/or prior to the patient 12 leaving the medical care area 100. At each step, a prompt can pop up on the touchscreen monitor 112 and the prompt must be confirmed before the safe surgical checklist proceeds and/or before the image taken or recalled by the image and video capture and recording device 108 can be shown on the touchscreen monitor 112.

An example of a safe surgical checklist that is completed in step 195 is as follows, with each successive step being introduced only after the previous step is confirmed:
1. Is the identity of the patient confirmed?
2. Is the procedure to be performed confirmed?
3. Is the site of the procedure confirmed?
4. Is the consent of the patient confirmed?
5. Is the site marked?
6. Are the anesthesia machine and medication check complete?
7. Is the pulse oximeter on the patient and functioning?
8. Have you reviewed the allergies of the patient (if any)?

9. Is equipment and assistance available if there is a difficult airway or aspiration risk?

10. If there is a risk of greater than 500 ml of blood loss, are 2 IVs/central access and fluids planned?

11. Have all team members introduced themselves by name and role before incision (which can be saved as an audio file with the safe surgical checklist)?

12. Has the name, procedure and site of incision been confirmed before skin incision?

13. If needed, has antibiotic propyhlaxis been given within the last 60 minutes?

14. Has sterility (including indicator results) been confirmed?

15. If applicable, is essential imaging displayed?

16. Has the nurse verbally confirmed the name of the procedure (which can be saved as an audio file with the safe surgical checklist)?

17. Has the nurse verbally confirmed completion of instrument, sponge and needle counts (which can be saved as an audio file with the safe surgical checklist)?

18. Have all specimens been labeled correctly?

19. Are there any equipment problems that need to be addressed (with the safe surgical checklist potentially including a further checklist and/or an automated report if answered "yes")?

After the safe surgical checklist is completed at step 195, the safe surgical checklist can be saved at step 196. It is contemplated that each step in the safe surgical checklist can be accompanied with an audio alert. It is contemplated that the safe surgical checklist can be processed and saved in steps 195 and 196 under voice control (e.g., using the voice-responsive control system (VCS) of the image and video capture and recording device 108). It is further contemplated that the safe surgical checklist can be saved at step 196 with a signature (e.g., a typewritten signature or an audio file). Moreover, it is contemplated that each step of the safe surgical checklist can be saved (with or without a signature) to be reviewed for potential errors.

After the patient record is retrieved in step 193 in the illustrated example, the patient record can also be reviewed at step 197. The patient record can include conclusive identification information (including a picture used in steps 194 and/or 195), a problem list (e.g., a list of pre-existing conditions), allergies and allergens, a history of surgeries, a list of current medications being taken by the patient 12, vitals and measurements of the patient 12, diagnostics, lab results, microbiology results and pathology results. The above list is not exhaustive and is for illustrative purposes only. The review of the patient record at step 197 can be conducted to ensure that actions that would be dangerous to the patient 12 are not performed and an updated patient record can be reviewed to ensure that such actions are not taken. It is contemplated that the step 195 of conducting the safe surgical checklist could include the step 197 of reviewing the patient record. Therefore, the surgeon and/or other medical personnel will be aware of the current medical information of the patient 12 (e.g., medications taken and problems that occurred since the surgery was scheduled) along with being aware of the complete medical information of the patient 12 (e.g., information for problems not related to the current procedure (for example, the cardiovascular history of the patient 12 when the procedure is an orthoscopic procedure)).

If any portion of the patient record is changed or if anything is added thereto (e.g., images, operative notes, etc.), the changes to the patient record can be saved at step 198. It is contemplated that any part of the patient record can be accessed and viewed and/or saved during steps 197 and 198 under voice control (e.g., using the voice-responsive control system (VCS) of the image and video capture and recording device 108) and can be stored locally in the computer system (e.g., of the image and video capture and recording device 108) during the procedure for easy access and before making critical decisions. The patient record can also be stored in the database of patient records 176 at any time (including after the procedure is completed).

Visual Indication of Information Flow Out of a Medical Care Area

The medical or surgical center 8 can include a teleconferencing and broadcasting system 200 for allowing communication between the medical care area 100 and other areas of the medical or surgical center 8 or areas outside of the medical or surgical center 8. An aspect of the present invention is to provide a system for providing a visual indication within the medical care area 100 when information is being recorded or transmitted outside of the medical care area 100.

Figure 14:
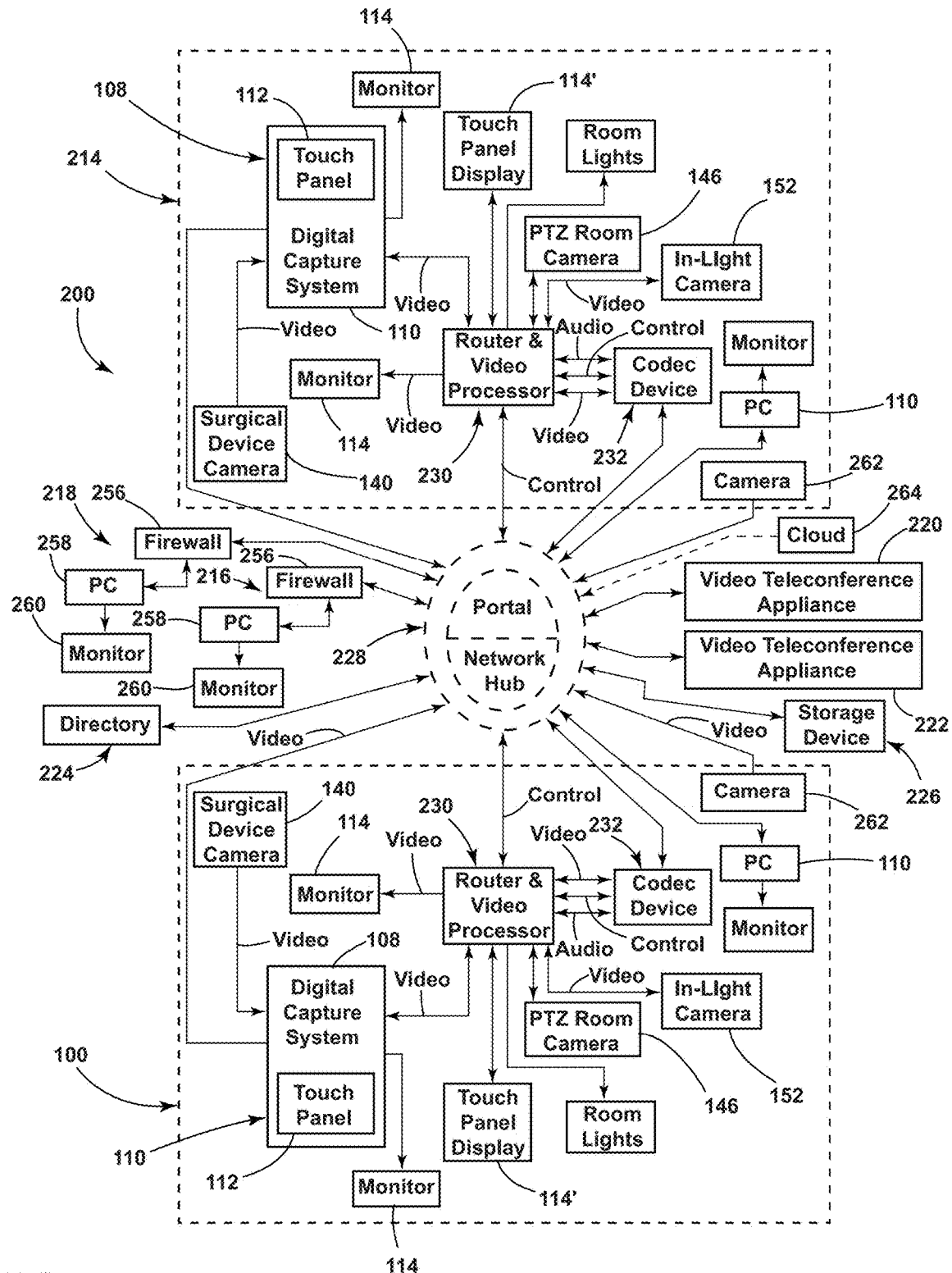
FIG. 14 is a schematic view of a teleconferencing and broadcasting system of the present invention.

FIG. 14 is a schematic view of the teleconferencing and broadcasting system 200 of the present invention for use in the medical or surgical center 8. FIG. 14 shows a first medical room 100 in the medical or surgical center 8, a second medical room 214 in the medical or surgical center 8, a first personal computing system 216, a second personal computing system 218, a first video teleconferencing appliance 220, a second video teleconferencing appliance 222, a directory 224 and a storage device 226, all connected to each other through a network hub and portal system 228. The teleconferencing and broadcasting system 200 allows the first medical room 100, the second medical room 214, the first personal computing system 216, the second personal computing system 218, the first video teleconferencing appliance 220, and the second video teleconferencing appliance 222 to selectively communicate with each other. While a first medical room 100 and a second medical room 214 are shown, it is contemplated that any number of medical rooms (including only one medical room) could be engaged with the network hub and portal system 228. Furthermore, while the first personal computing system 216 and the second personal computing system 218 are shown, it is contemplated that any number of personal computing systems (including no personal computing system or only one personal computing system) could be engaged with the network hub and portal system 228. Moreover, while the first video teleconferencing appliance 220 and the second video teleconferencing appliance 222 are shown, it is contemplated that any number of video teleconferencing appliances (including no video teleconferencing appliances or only one video teleconferencing appliance) could be engaged with the network hub and portal system 228. It is contemplated that the video conferencing appliances could be offsite codecs to provide support for videoconferencing at offsite locations. It is noted that all the communications between the network hub and portal system 228 and the medical rooms can take place over a local area network (LAN), with the communications between any of the video teleconferencing appliances 220, 222 also taking place over the LAN. Alternatively, it is contemplated that communications with any of the video teleconferencing appliances 220, 222 can take place over the internet or using any other communication scheme.

In the illustrated example, the first medical room 100 and/or the second medical room 214 could be an operating room wherein a medical procedure could be taking place. Alternatively, the first medical room 100 and/or the second medical room 214 could be other rooms in the medical or surgical center 8 (e.g., pathology lab, hospital conference room, hospital training room, diagnosis room or patient room). The first personal computing system 216 and the second personal computing system 218 could be located anywhere (e.g., inside the medical or surgical center 8 (and connected to the LAN) or elsewhere). Likewise, the first video teleconferencing appliance 220 and the second video teleconferencing appliance 222 could be located anywhere (e.g., inside a medical facility or elsewhere).

Each of the illustrated first medical room 100 and the second medical room 214 can include a plurality of communication and diagnostic devices therein. The first medical room 100 and the second medical room 214 can include a media router and video processor 230. The media router and video processor 230 can include software and hardware that includes support for a codec device 232 and that interacts with the network hub and portal system 228. The media router and video processor 230 can also include an integrated or separate control system for controlling the media router and video processor 230. The media router and video processor 230 includes a video processor for processing video signals sent to and received from the codec device 232. Further, the media router and video processor 230 can receive video streams including a video stream from a video camera 140 (e.g., a camera of an endoscope), stream from a pan-tilt-zoom (PTZ) room camera 146 located within the first medical room 100 and the second medical room 214, and a stream from an in-light video camera 152 located within the overhead light 154 of the first medial room 100 and the second medical room 214. The media router and video processor 230 can select a video stream that is sent to the codec device 232 connected thereto for broadcast over the LAN or Internet or other communication scheme (via the network hub and portal system 228). Further, the media router and video processor 230 can scale up or down video signals received thereat. For example, high definition (HD) video signals can be scaled down to standard definition video signals. The media router and video processor 230 also controls a position of the PTZ room camera 146 located in the first medical room 100. The first medical room 100 and the second medical room 214 can include the additional monitor 114 and/or a touch panel display monitor 114' upon which are selectively displayed: camera images or video streams received from the video camera 140, from the in-light video camera 152 or from the PTZ room camera 146 located in the same medical room 100. Further, external video streams received via another codec device 232 can be displayed on the additional monitor 114 connected to the media router and video processor 230. An example of the media router and video processor 230 can be the SWITCHPOINT INFINITY® 3 system of the Assignee hereof. An example of a control system for the media router and video processor 230 can be the SWITCHPOINT INFINITY® 3 control system of the Assignee hereof.

In the illustrated example, the codec device 232 encodes video and audio streams received from the media router and video processor 230 and transmits same over a network, such as the LAN or the Internet, for use by other viewing devices. The codec device 232 can simultaneously output H.264 encoded video streams having different resolutions 720p, 480p or can output a single 1080i video stream. The illustrated codec device 232 is also capable of receiving and outputting high definition video streams, such as 1080i, 720p, 480p at appropriate band widths for streaming to multiple devices. Furthermore, the codec device 232 can decode and decompress an encoded audio and video stream received from another codec device 232 unit over the network. The codec device 232 provides a decoded video stream from the network to the media router and video processor 230 for use and display thereby. The codec device 232 is capable of simultaneously encoding and compressing video signals received from the media router and video processor 230 for output over the network, while decoding and decompressing video streams received over the network from a different codec device 232.

Internet protocols of the illustrated codec device 232 include application layers Real-Time Transport Protocol (RTP), RTP control protocol (RTCP) and Real-Time Streaming Protocol (RTSP) for the video stream; and secure shell (SSH) for secured communication. As for transport layers, the codec device 232 can use Real-Time Transport Control Protocol (TCP) as a transport layer for SSH and User Datagram Protocol (UDP) as a transport layer for RTP, RTCP and RTSP application layers. The codec device 232 can include an encoder that time stamps data packets and determines a sleep time for each data packet.

The illustrated codec device 232 can encode real-time video streams using the MPEG-4 AVC (H.264) standard and can encode audio streams utilizing the AAC standard. The codec device 232 can also perform data encryption and decryption. The codec device 232 encoders and decoders can include multiple microprocessors and hardware circuitry that perform video and audio signal processing. The codec device 232 can include converters, RS-232 connections, audio, USB and Ethernet ports or connectors for both the encoder and decoder. The codec device 232 can receive a DVI-D video stream from the media router and video processor 230 and convert same to an HDMI signal. The codec device 232 can convert the HDMI signal and an audio signal to an SDI signal that is provided to at least one encoder. The codec device 232 encoders can receive an RS-232 control signal from the media router and video processor 230 to compress and encode the SDI signal. The encoders can output an encrypted video stream to the network or "cloud" in H.264 format over a RJ45 ethernet connection.

The encoders of the illustrated codec device 232 can perform data compression of the video stream and audio stream while encoding the streams. Depending on the control signals provided to the encoder by the media router and video processor 230, the codec device 232 may output an encrypted compressed video stream having a 1080i resolution and an audio stream. A different control signal from the media router and video processor 230 enables the codec device 232 to encode and output a pair of video streams having different resolutions 720p, 480P simultaneously. The encoder can utilize the same codec or algorithm for encoding and compressing the video and audio streams regardless of the chosen video resolution. The 720p video stream can be output as a RTSP unicast transport stream and the 480p video stream can be output as a multi-cast UDP stream.

The illustrated codec device 232 can include decoders that operate in a reverse manner to the encoder. In operation, a decoder of the codec device 232 receives an encrypted, encoded, compressed digital video and audio stream provided in H.264 format by another codec device 232 via the network or from a "cloud" 264 as passed along by the network hub and portal system 228. The selected decoder can decrypt and decode the received H.264 video stream and audio stream into an SDI signal. The SDI signal is provided to an SDI to HDMI converter that outputs an HDMI signal and an audio stream. Then, the HDMI video signal is converted into a DVI-D format and output along with the audio stream to the media router and video processor 230 for display. With regard to incoming video streams, the selected decoder may be configured to only decode an incoming compressed, encoded video stream received from another codec device 232. The decoder can be selected depending on the resolution of the encoded video stream received or chosen for processing. The decoders can operate using the same codec as the encoder.

In the illustrated example, the network hub and portal system 228 can be installed on a network server and can provide status information and details, such as IP addresses, that may be required for the codec devices 232 to communicate with each other. The network hub and portal system 228 can maintain a list of codec devices 232 available in a network and can enable one-to-one communication between codec devices 232. The network hub and portal system 228 can also maintain a list of video streams and auxiliary video streams for reading and display by the computer system having monitors disposed at various remote locations or the computer systems 110 having monitors within the first medical room 100 and/or a second medical room 214 provided with the media router and video processor 230. Audio streams can be provided with each of the video streams.

The illustrated network hub and portal system 228 can also provide a web based portal for enabling a plurality of PCs to make calls and teleconference with other PCs, which may include the computer system 110 located in the first medical room 100 and/or a second medical room 214 with the media router and video processor 230 for use therewith. Users of the computer systems 110 or the personal computers (PCs) 258 can interact with the network hub and portal system 228 through their web browsers/web pages. The network hub and portal system 228 authenticates users and allows them to browse the video streaming list for computer systems and PCs and the video streams of the codec system 232. For example, users of the computer system 110 and the PCs 258 on a hospital network can browse video stream lists, select a stream to view and watch the video stream. The network hub and portal system 228 may combine up to a plurality of video streams, including a plurality of video signals from the codec device 232, for transmission as a single video image composition to various display devices. Thus, a plurality of video streams can be multi-viewed on the monitors of the computer systems 110 or the monitors 260 of the PCs 258 for teleconferencing. The display devices may include PCs with web cams that output their own video stream, and other PC devices that can only select and watch video streams. The network hub and portal system 228, via the media router and video processor 230, can allow a remote user with the PC 258 to remotely control the PTZ room camera 146. Further, the network hub and portal system 228 can allow a remote user of the PC 258 to view, after control selection at the media router and video processor 230 of an output by a corresponding codec device 232, a video stream from one of the PTZ room cameras 146, the video camera 140 or the in-light camera 152.

In the illustrated example, the computer system 110 and the monitor are provided in a room with the media router and video processor 230 for teleconferencing. The computer system 110 can receive a web page with plural video streams directed by the network hub and portal system 228 that the computer system 110 displays on the monitor. Furthermore, the network hub and portal system 228 can direct selected audio streams to the computer system 110. Thus, the computer system 110 can provide multi-view images to enable teleconferencing for a user that is also operating the media router and video processor 230 connected to the codec device 232 in the same medical room 100, 214. The computer system 110 and the monitor can obtain HD codec video stream from the codec device 232 over the network via the network hub and portal system 228.

The illustrated first medical room 100 and the second medical room 214 can include the image and video capture and recording device 108 that captures and records video streams or still images from the video camera 140. The image and video capture and recording device 108 can include the touch panel 112 (which can be a display or can include an additional display 114 in addition to the touchscreen monitor 112). A user can change video compression and other properties of the image and video capture and recording device 108. The image and video capture and recording device 108 can save video to a disc or provide same to the IP network as a unicast video stream having UDP type packets and a variable bitrate. Image storage and video operations can be controlled by a wireless hand-held remote control, a surgical device camera head button, or the touch panel 112. The image and video capture and recording device 108 can broadcast video streams over the network.

In the illustrated example, the remote storage device 226 can be connected to the hospital network for providing stored video streams to the computer system 110 and the image and video capture and recording device 108 for viewing. The remote storage device 226 can obtain and store video streams output by the image and video capture and recording device 108. The remote storage device 226 can also include any of the databases outlined above. An in-room camera 262 can provide video from the first and second medical rooms 100, 214 over the medical facility network or Internet so that users at a remote location may determine the status of the medical room 100, 214. The in-room camera 262 can connect directly to the hospital network. A firewall 256 can be provided between the hospital network and remote PCs 258 or other remote devices on an IP network.

An aspect of the present invention is to provide a visual indication if any video, audio and/or text information within one of the rooms 100, 214 is being recorded or transmitted outside of the room 100, 214. For example, a visual indication can be presented when video, audio and/or text information is being recorded by the image and video capture and recording device 108 and/or when video, audio and/or text information is being broadcast from inside one of the rooms 100, 214 to a location outside of the room 100, 214 (e.g., to another room 214, to a PC 258, to the first video teleconferencing appliance 220 or the second video teleconferencing appliance 222. When there is a visual indication that the video, audio and/or text information is being recorded or transmitted outside of the room 100, 214, the surgical care team will be able to quickly and intuitively understand what information in the room 100 is being recorded and/or transmitted outside of the room 100. Such knowledge can be useful in order to comply with HIPAA and for general patient privacy. Moreover, there may be times during a medical or surgical procedure when the surgical care team would like to stop recording and/or transmission of information temporarily and the visual indication will easily allow the surgical care team to know when the information is being recorded and/or transmitted and when recordation and/or transmission is stopped.

Figure 15:
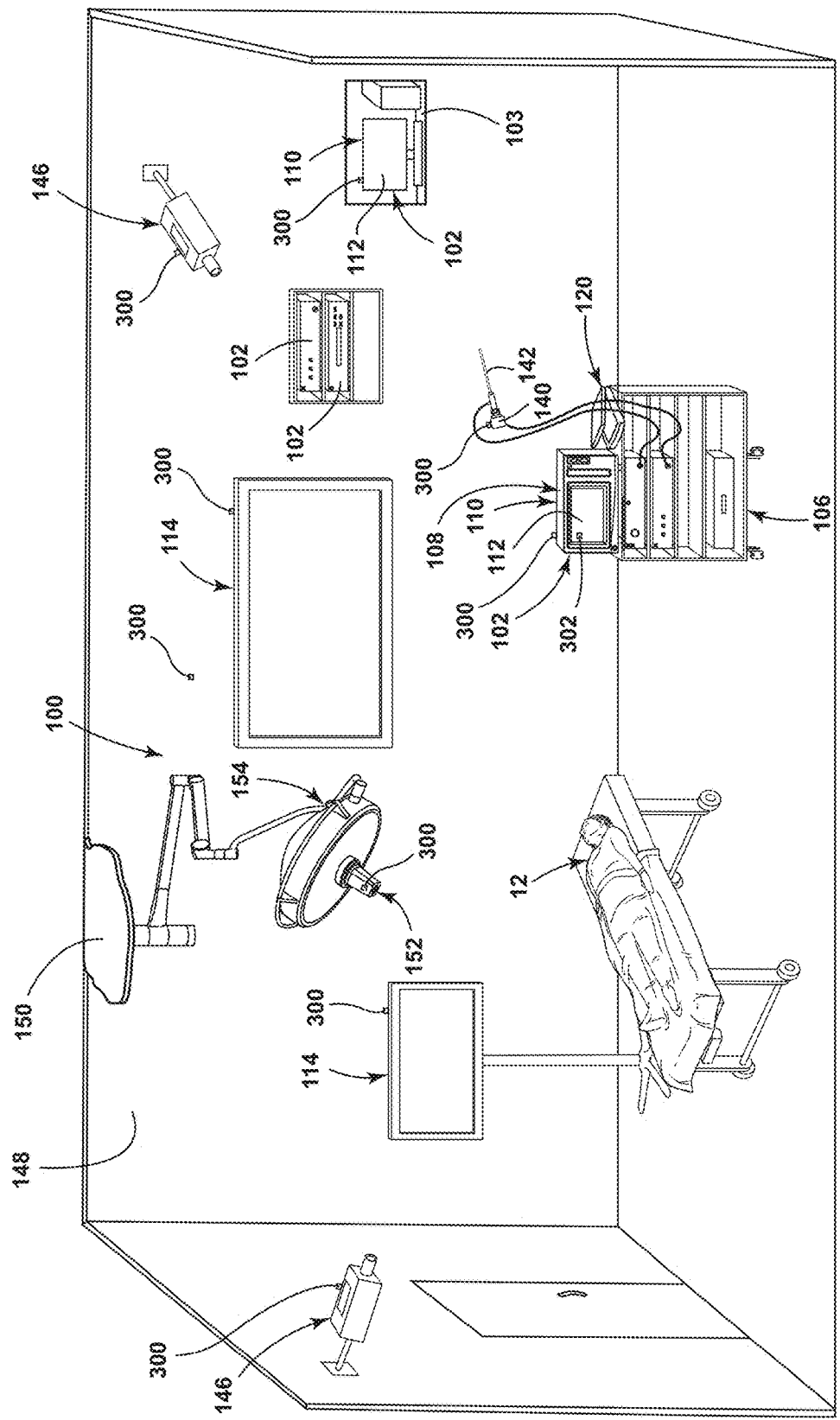
FIG. 15 is a perspective view of an operating room illustrating medical devices used with the teleconferencing and broadcasting system of the present invention.

In addition to providing a visual indication when any video, audio and/or text information within one of the rooms 100, 214 is being recorded or transmitted outside of the room 100, 214, an aspect of the present embodiment is to provide an easy control or toggle switch (e.g., the GUI 302 on the touchscreen monitor 112 of the image and video capture and recording device 108 as illustrated in FIG. 15) that can toggle the state of all information (video, audio and/or text information) being recorded and/or broadcast simultaneously. Therefore, when the control or toggle switch is activated a first time, all information is prevented from being recorded or broadcast and a second activation of the control or toggle switch will allow the recordation and/or broadcast of all information. It is contemplated that the control or toggle switch can be programmed to prevent all patient personal information from being saved or broadcast, but allow other information to be saved or broadcast. For example, an image within an incision could be saved or broadcast, but the identity of the patient could be prevented from being saved or broadcast. The control or toggle switch could be any physical control or switch (e.g., a press button) or a virtual switch (e.g., an icon on one of the computer systems 110). An example of a virtual switch that can be activated to enter a privacy mode (wherein recordation and/or broadcasting is prevented) is disclosed in U.S. Pat. No. 9,258,522 entitled PRIVACY SETTING FOR MEDICAL COMMUNICATIONS SYSTEMS, the entire contents of which are hereby incorporated herein by reference. Moreover, it is contemplated that the control or toggle switch could be a voice command that allows or prevents information from being recorded or broadcast. The control or toggle switch could be any combination of a physical control or switch, a virtual control or switch and/or an audible control or switch. When the toggle or control is activated, it is contemplated that any personal information could be removed automatically from information being broadcast or recorded, but with the remainder of the information (e.g., image) continuing to be broadcast or recorded. For example, when the toggle or control is activated, all patient information in text form can be removed from an image.

In the illustrated example, a first method of providing a visual indication that information is being recorded or broadcast includes providing lights 300 that are illuminated when information is being recorded or broadcast. As illustrated in FIG. 15, the computer systems 110 can each have the light 300 thereon (e.g., on the image and video capture and recording device 108), the additional monitors 114 can each have the light 300 thereon, the room cameras 146 can have the light 300 thereon, the camera 152 on the overhead light 154 can have the light 300 thereon (or elsewhere on the overhead light 154), and the video camera 140 connected to the endoscope 142 can have the light 300 thereon. It is contemplated that the room 100 itself can have a light 300 (e.g., on the wall 148 as shown or on the ceiling 150). It is contemplated that any item in the room 100 could have the light 300 thereon. Furthermore, it is contemplated that only some of the devices in the room 100 could have the light 300 thereon (e.g., only on the display devices such as the touchscreen monitor 112 and the additional monitors 114). However, the light 300 can be on multiple objects in the room 100. While the visual indication that information is being recorded or broadcast is shown as including lights 300, it is contemplated that any visual indication could be used in addition to the lights 300 or in place of the lights 300. It is further contemplated that a microphone could have a light 300 thereon that is illuminated if the audio in the room is being recorded and/or broadcast.

In the illustrated example, all of the lights 300 are illuminated when information is being recorded and/or broadcast as outlined above. Contrarily, it is contemplated that the lights 300 could be illuminated when information is not being recorded and/or broadcast and not illuminated when information is being recorded or broadcast. It is contemplated that the lights 300 could be any device that provides illumination (e.g., an LED or an incandescent bulb). Moreover, it is contemplated that the lights 300 could emit any wavelength of visible light (e.g., red). It is further contemplated that each light 300 could include a plurality of visible indicators (e.g., multiple LEDs) or each device would include a plurality of lights, with each indicator (or separate light) providing an indication of different information (e.g., levels of privacy). For example, the light 300 could emit a first color of light (e.g., green) when nothing is being recorded and/or broadcast, a second color of light (e.g., blue) when the information is only being locally recorded, and a third color of light (e.g., red) when the information is being recorded to an external location and/or is being broadcast. It is contemplated that the first color could be illuminated when the recording and/or broadcasting is to a destination that is HIPPA compliant and the second color could be illuminated when the recording and/or broadcasting is to a destination that is not HIPPA compliant or is to a destination which is unknown if it is HIPPA compliant. In addition to the lights 300, it is contemplated that a light could be seen by medical personnel in wearable technology that provides an image on glasses (e.g., Google Glass sold by Google Inc. of Mountain View, Calif.), could be on items worn by the medical personnel and viewable by other people in the room 100 (e.g., a light worn on clothing), could be on the walls 148, could be on any device (e.g., on a shaving device) or could be anywhere else in the room 100.

Figure 16A:
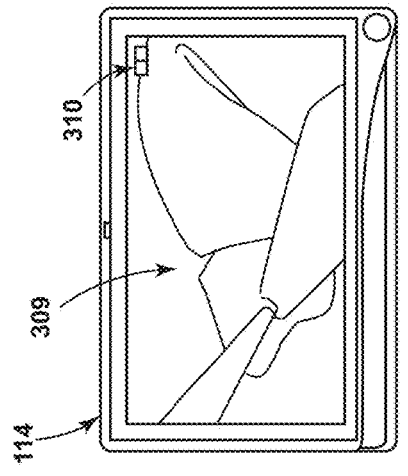
FIGS. 16A-16E illustrate monitors having indications thereon indicating that recording or broadcasting is taking place according to an aspect of the present invention.
Figure 16B:
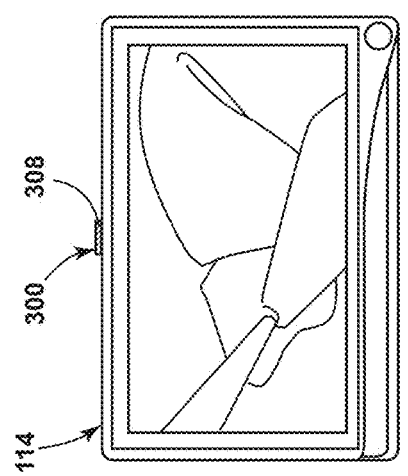

FIGS. 16A and 16B illustrate lights 300 on additional monitors 114. The lights 300 could also be on similar locations on the touchscreen monitor 112 of the image and video capture and recording device 108. FIG. 16A illustrates the light 300 as an LED 306 located on a bezel 307 surrounding a screen 309 of the additional monitor 114. The LED 306 (or plurality of LEDs) could be located anywhere on the bezel 307 (e.g., on the top as shown or on a chin extending downward at the bottom of the bezel 307). The LED 306 (or plurality of LEDs) could also be located on a module that connects to the additional monitor 114. FIG. 16B illustrates the light 300 as a projection 308 extending upward from the top of the additional monitor 114. The projection 308 can provide up to 360° of illumination and can extend from any surface of the additional monitor 114 (or the touchscreen monitor 112 of the image and video capture and recording device 108) or any other device connected thereto.

Figure 16C:
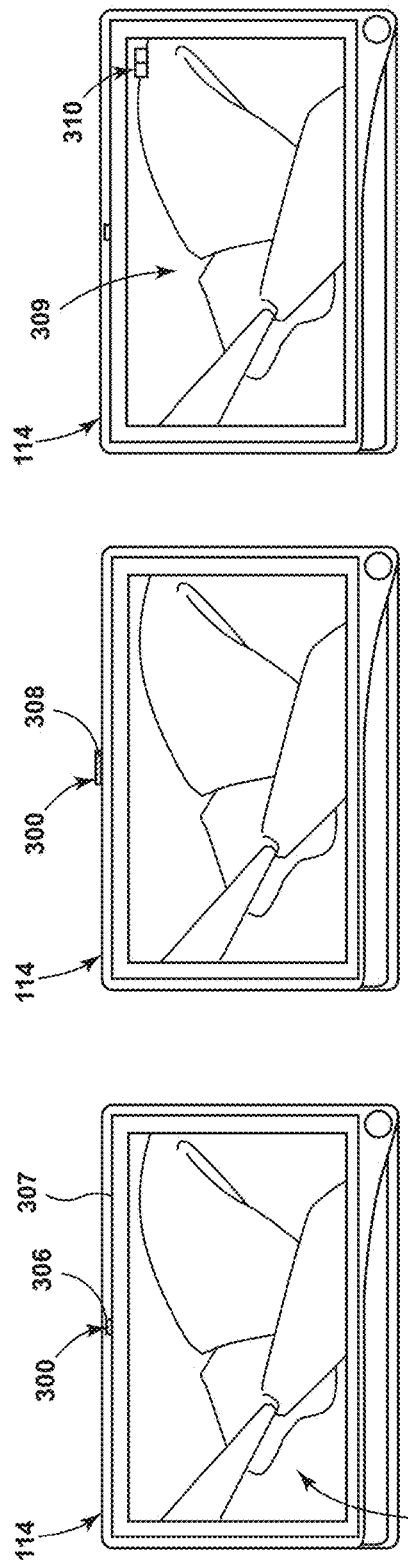
Figure 16E:
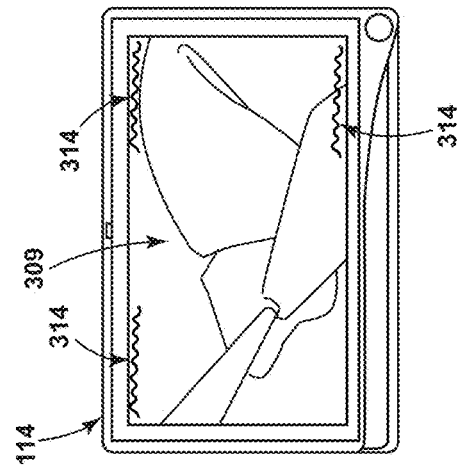
Figure 16D:
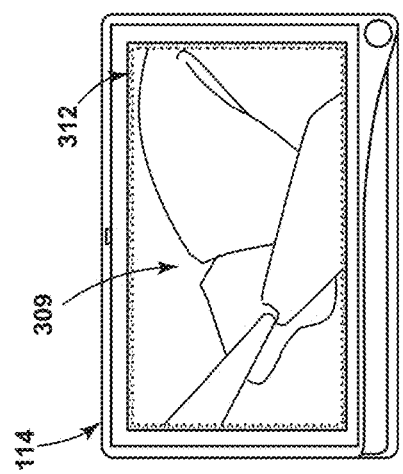

In the illustrated example, a second method of providing a visual indication that information is being recorded or broadcast includes providing a visual indication directly onto the image on the screen 309 of the additional monitor 114 or on the touchscreen monitor 112 of the image and video capture and recording device 108. FIGS. 16C-16E illustrate methods of providing a visual indication that information is being recorded or broadcast by providing a visual indication onto the image on the screen 309. In FIG. 16C, a color block 310 is superimposed onto the image on the screen 309. The color block 310 can be on any (or all) additional monitor 114 or touchscreen monitor 112 showing the image and can be located in any position on the additional monitor 114 or touchscreen monitor 112 (including to a side of the image and not superimposed thereon). FIG. 16D illustrates a colored halo 312 on a periphery of the screen 309 that is illuminated to provide a visual indication that information is being recorded or broadcast. FIG. 16E illustrates text 314 on the image, wherein the color of the text can change (e.g., turn red) to provide a visual indication that information is being recorded or broadcast or to provide an indication of the destination of the text (and image if the text is superimposed onto an image). In all of the visual indicators in FIGS. 16C-16E, the color can be of a single color that is either on or off to indicate that information is being recorded or broadcast or can change color to indicate the level of privacy as outlined above. It is contemplated that the second method of providing a visual indication could include superimposing a logo or other on screen graphic, with the shape and/or color of the logo or other on screen graphic (or absence thereof) providing the visual indication that information is being recorded or broadcast.

Recording Information on a White Board in an Operating Room

During medical or surgical procedures in an operating room, a whiteboard 400 (FIG. 17) is often used to keep track of important information. An aspect of the present invention is to provide a simple manner of recording the information on the whiteboard 400.

Figure 17:
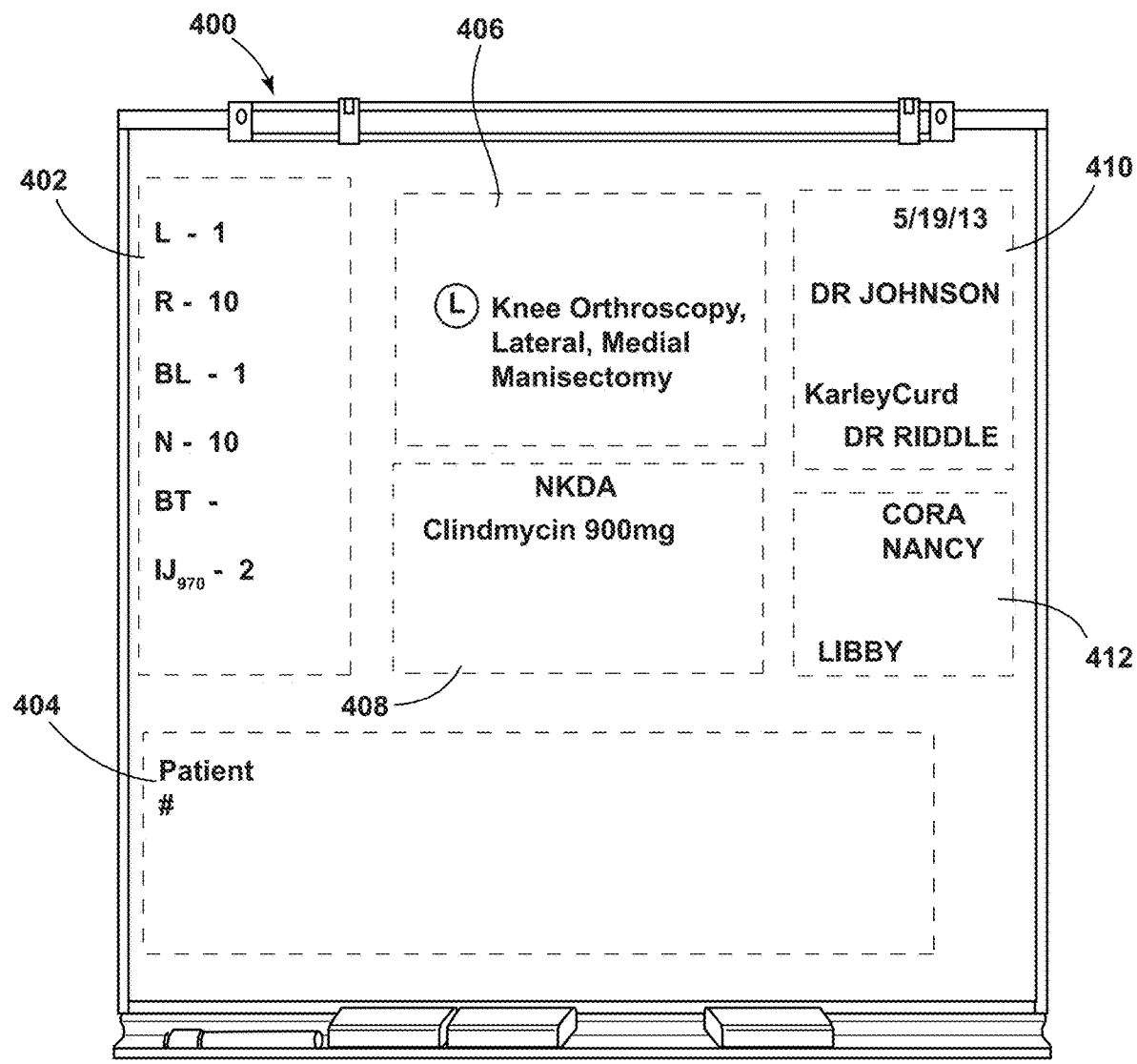
FIG. 17 is a whiteboard used in a medical procedure of the present invention.
Figure 18:
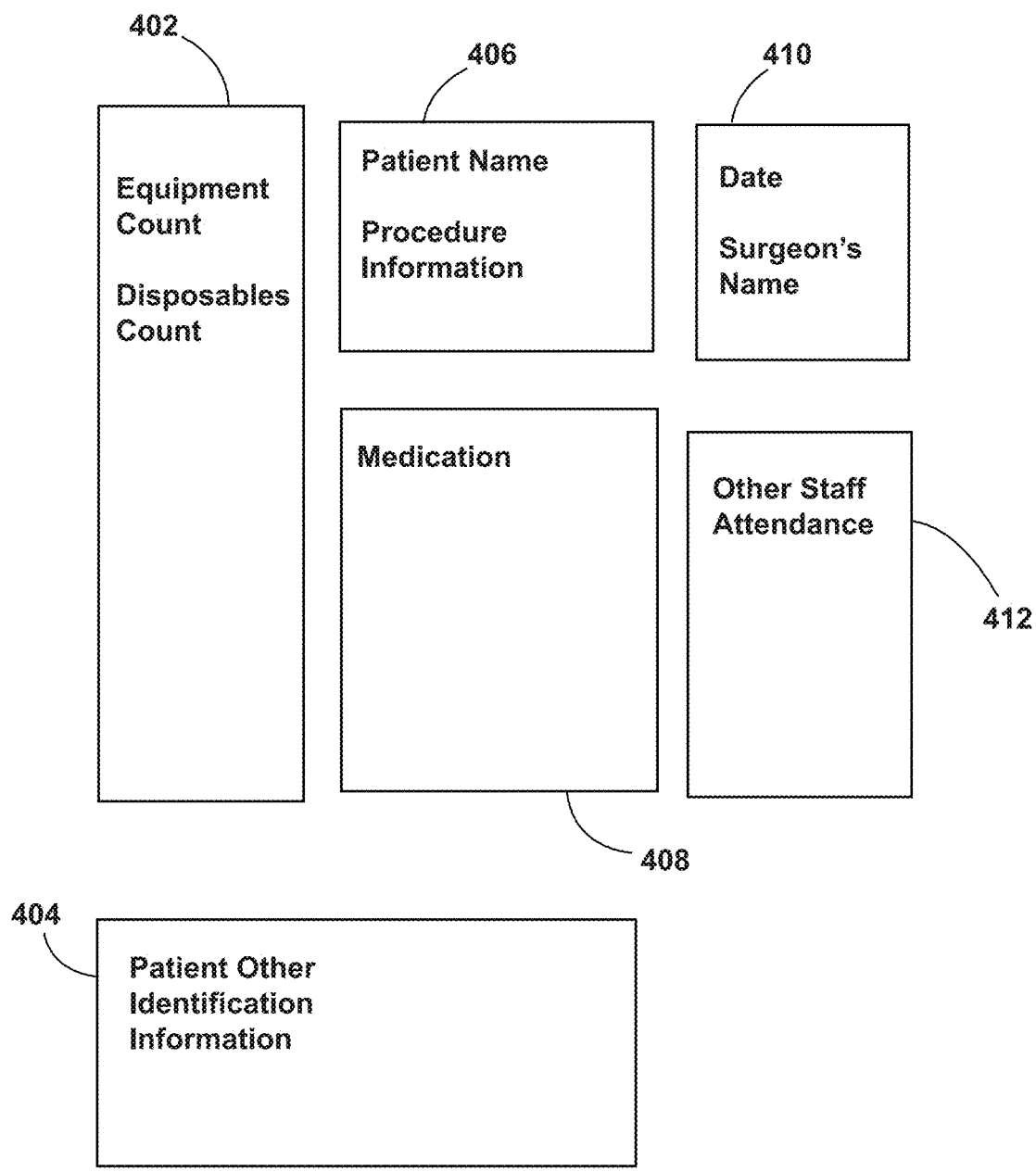
FIG. 18 is a representation of the whiteboard used in the medical procedure of the present invention.

As illustrated in FIG. 17, the information written on the whiteboard 400 is grouped together in certain areas, with each area including a particular type of information. For example, the whiteboard 400 can include equipment count and disposable count information in a first area 402, other patient identification information (e.g., a patient number) in a second area 404, patient name and procedure information in a third area 406, medication administered in a fourth area 408, date and a surgeon's name in a fifth area 410 and other staff attendance in a sixth area 412. It is contemplated that the areas on the whiteboard 400 can encompass any area and include any desired information. FIG. 17 includes examples of actual information written on the whiteboard 400 and FIG. 18 includes the areas with the type of information within the areas.

In the illustrated example, the whiteboard 400 can be scanned (e.g., using a room camera 146 or a cell phone camera communicating with one of the computer systems 110) and text information in the scanned image can be obtained using image processing software and algorithms including optical character recognition, image normalization (e.g., using histogram equalization and/or color removal), feature extractions (e.g., line segment and edge detection) and/or pattern classification as is well known to those skilled in the art. The information on the whiteboard 400 can then be saved and stored on a remote or external patient record database communicating with the computer system 110 or on a local database (permanently or temporarily) of the computer system 110. It is contemplated that the information can be saved along with the category of information (e.g., equipment count and disposables count) for easy reference after the medical or surgical procedure. It is further contemplated that the computer system 110 could include software (e.g., optical character recognition software and logic software) that can identify the type or category of information in each area from the text in each area and automatically save the text along with the type or category of information. It is contemplated that the areas 402, 404, 406, 408, 410 and 412 can be entered into the computer system 110 as a template using the template creation process outlined above for creating the database of identification card templates and wristband templates.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of controlling distribution of patient information during a medical procedure on a patient, the method comprising, at a computing system and during the medical procedure on the patient:
   receiving surgical images or video from at least one camera located in the medical room;
   displaying patient information on at least one display located in the medical room, the patient information comprising the surgical images or video;
   at least one of: (a) transmitting the patient information to at least one display located in a location other than the medical room, and (b) recording the patient information;
   activating one or more visual indications located in the medical room when the patient information includes patient personal information that can identify the patient to notify the at least one medical personnel in the medical room that the patient personal information is being recorded and/or transmitted to the at least one display located in the location other than the medical room;
   receiving a user command, responsive to the one or more visual indications, to cease the recording of the patient personal information and/or the transmitting of the patient personal information to the at least one display located in the location other than the medical room; and
   in response to receiving the user command and while continuing to display the patient information, including the patient personal information, on the at least one display located in the medical room:
   in accordance with the patient information being recorded, ceasing recording of the patient personal information while continuing to record the surgical images or video, and
   in accordance with the patient information being transmitted to the at least one display located in the location other than the medical room, ceasing transmission of the patient personal information to the at least one display located in the location other than the medical room while continuing to transmit the surgical images or video to the at least one display located in the location other than the medical room; and
   deactivating the one or more visual indications, thereby indicating to the at least one medical personnel in the medical room that the patient personal information is no longer being recorded and/or transmitted to the at least one display located in the location other than the medical room.

2. The method of claim 1, wherein the one or more visual indications are lights.

3. The method of claim 2, wherein the lights are located on the at least one display in the medical room.

4. The method of claim 3, wherein the lights are also located on at least one recording device in the medical room.

5. The method of claim 4, wherein the lights are also located on the at least one camera.

6. The method of claim 2, wherein the lights are located on the at least one recording device.

7. The method of claim 2, wherein the lights are configured to illuminate at a plurality of colors.

8. The method of claim 7, wherein a first color of the plurality of colors indicates that the patient personal information is being recorded, and
   a second color of the plurality of colors indicates that the patient personal information is being transmitted to the at least one display located in the location other than the medical room.

9. The method of claim 1, wherein the one or more visual indications are superimposed over an image on the at least one display in the medical room.

10. The method of claim 1, comprising saving the patient information to a storage device located remotely from the medical room.

11. The method of claim 1, comprising saving the patient information to at least one recording device located in the medical room.

12. The method of claim 1, wherein the user command is received from the at least one medical personnel located in the medical room.

13. The method of claim 1, comprising, in response to receiving a subsequent user command, starting the recording and/or transmitting of the patient personal information.

14. The method of claim 13, wherein the user command comprises one or more of an interaction with an icon on a graphical user interface (GUI) on the display in the medical room, an interaction with a button press, and a voice command.

15. The method of claim 1, wherein the at least one camera comprises at least one of a video camera, X-ray scanner, digital X-ray acquisition apparatus, fluoroscope, computed tomography (CT) scanner, magnetic resonance imaging (MRI) scanner, and ultrasound scanner.

16. The method of claim 1, wherein the patient information is transmitted to the at least one display located in the location other than the medical room for teleconferencing.

17. The method of claim 1, wherein the location other than the medical room includes one or more of an operating room, a pathology lab, a hospital conference room, a hospital training room, a diagnosis room, and a patient room.

18. The method of claim 1, wherein the patient personal information comprises text.

* * * * *